(12) United States Patent
Zhou et al.

(10) Patent No.: US 9,039,181 B2
(45) Date of Patent: May 26, 2015

(54) LARGE DIOPTER RANGE REAL TIME SEQUENTIAL WAVEFRONT SENSOR

(71) Applicant: Clarity Medical Systems, Inc., Pleasanton, CA (US)

(72) Inventors: Yan Zhou, Pleasanton, CA (US); William Shea, Pleasanton, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 0 days.

(21) Appl. No.: 14/496,172

(22) Filed: Sep. 25, 2014

(65) Prior Publication Data

US 2015/0049305 A1    Feb. 19, 2015

Related U.S. Application Data

(60) Continuation of application No. 14/187,133, filed on Feb. 21, 2014, now Pat. No. 8,857,985, which is a continuation of application No. 13/745,738, filed on Jan. 18, 2013, now Pat. No. 8,678,591, which is a continuation of application No. 13/198,442, filed on Aug. 4, 2011, now Pat. No. 8,356,900, which is a continuation-in-part of application No. 12/790,301, filed on May 28, 2010, now Pat. No. 8,579,437, which is a division of application No. 11/761,890, filed on Jun. 12, 2007, now Pat. No. 7,815,310, which is a continuation-in-part of application No. 11/335,980, filed on Jan. 20, 2006, now Pat. No. 7,445,335.

(51) Int. Cl.
*A61B 3/10* (2006.01)
*G02B 17/08* (2006.01)

(52) U.S. Cl.
CPC .......... *A61B 3/1015* (2013.01); *G02B 17/0896* (2013.01)

(58) Field of Classification Search
CPC ...... A61B 3/10; A61B 3/1005; A61B 3/1015; A61B 3/103; A61B 3/107; A61B 3/117; A61B 3/1173; A61B 3/14; A61B 3/15; G02B 15/163; G02B 13/0095; G02B 23/2446
USPC ......... 351/205, 206, 210, 212, 214, 221, 246; 359/434, 676
See application file for complete search history.

(56) References Cited

U.S. PATENT DOCUMENTS 8,550,624 B2 * 10/2013 Padrick et al. ................ 351/205
2007/0070292 A1 * 3/2007 Liang ............................ 351/205

* cited by examiner

*Primary Examiner* — Huy K Mai
(74) *Attorney, Agent, or Firm* — Kilpatrick Townsend and Stockton LLP

(57) ABSTRACT

Example embodiments of a large dynamic range sequential wavefront sensor for vision correction or assessment procedures are disclosed. An example embodiment includes first and second optically coupled 4F relays and a variable focus lens disposed substantially at the image plane of the first 4F relay and the object plane of the second 4F relay.

3 Claims, 19 Drawing Sheets

LARGE DIOPTER RANGE REAL TIME SEQUENTIAL WAVEFRONT SENSOR

RELATED APPLICATIONS

The present application is a continuation of U.S. Ser. No. 14/187,133 filed Feb. 21, 2014 (Allowed); which is a continuation of U.S. Ser. No. 13/745,738 filed Jan. 18, 2013 (now U.S. Pat. No. 8,678,591); which is a continuation of U.S. Ser. No. 13/198,442 filed Aug. 4, 2011 (now U.S. Pat. No. 8,356,900); which is a continuation-in-part application of U.S. Ser. No. 12/790,301 filed May 28, 2010 (now U.S. Pat. No. 8,579,437); which is a divisional of U.S. Ser. No. 11/761,890 filed Jun. 12, 2007 (now U.S. Pat. No. 7,815,310); which is a continuation-in-part of U.S. Ser. No. 11/335,980 filed Jan. 20, 2006 (now U.S. Pat. No. 7,445,335); the contents, all of which are incorporated herein by reference in their entirety for all purposes.

TECHNICAL FIELD OF THE INVENTION

One or more embodiments of the present invention relate generally to ophthalmic wavefront sensors and particularly relate to wavefront sensor modules and their attachment to or integration with an ophthalmic instrument for vision correction surgical procedures and to integration with ophthalmic instruments for vision assessment and or correction during surgical procedures.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which, in and of themselves, may also be inventions.

Wavefront sensors for ophthalmic applications are generally bulky and stand-alone desktop instruments. Although there have been attempts to integrate a wavefront sensor with an ophthalmic instrument such as a LASIK system (see for example, U.S. Pat. No. 6,685,319), a fundus camera (see for example, U.S. Pat. No. 6,572,230), and a confocal scanning laser ophthalmoscope (see for example, U.S. Pat. No. 7,057,806), these integrations are generally not aimed at maintaining the original ophthalmic instrument intact with the wavefront sensor as a separate compact module attached to or integrated with the ophthalmic instrument.

SUMMARY OF THE INVENTION

An example embodiment a wavefront relay optical apparatus comprises a first 4F optical relay including first and second lens and configured to relay a wavefront from a first object plane to a first image plane, a second 4F optical relay including third and fourth lenses configured to relay a wavefront from a second object plane to a second image plane, where the first and second 4F optical relays are disposed so that the second object plane and the first image plane are located at about the same position and a variable focal length lens positioned substantially at the second object plane and configured to change the sphero-diopter value of the wavefront when it is relayed from the first object plane to the second wavefront image plane.

In another example embodiment a large diopter range sequential wavefront sensor for vision correction or assessment procedures comprises a first optical wavefront relay system including first and second lenses, each lens having a diameter, a focal length and an optical axis, with the first optical wavefront relay system configured to relay an incident wavefront from a first object plane in a first object space to a first wavefront image plane in a first wavefront image space along a first beam path where the focal lengths and diameters of the first and second lenses are selected to guide an incident wavefront relay beam having a large diopter range at the first object plane to the first wavefront image plane, a second optical wavefront relay system including third and fourth lenses, each lens having a diameter, a focal length and an optical axis, with the second optical wavefront relay system having a second object plane in a second object space that is substantially at the first wavefront image plane, and configured to further relay the incident wavefront from the first wavefront image plane to a second wavefront image plane in a second wavefront image space along a second optical path, with the third lens configured to guide the wavefront relay beam to a Fourier transform plane located between the third and fourth lenses, a variable focal length lens disposed substantially at the second object plane in the second object space, with the variable focus length lens being substantially conjugate to the first object plane and the second wavefront image plane and configured to dynamically change the sphero-diopter value of the wavefront when it is relayed from the first object plane to the second wavefront image plane, a reflective beam shifting element disposed substantially at the Fourier transform plane located between the third and fourth lenses, positioned along the optical axis of the third lens to intercept substantially the entire wavefront relay beam over a desired large diopter range and oriented to fold the second optical path at a folding angle having a magnitude that prevents a wavefront beam reflected from being intercepted by the third lens, a wavefront sampling aperture positioned at or near the second wavefront image plane and an image spot position sensing device positioned behind the sampling aperture.

These and other features and advantages of the present invention will become more readily apparent to those skilled in the art upon review of the following detailed description of the preferred embodiments taken in conjunction with the accompanying drawings.

DETAILED DESCRIPTION

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure the present invention. Further, each appearance of the phrase an "example embodiment" at various places in the specification does not necessarily refer to the same example embodiment.

In a typical wavefront sensor used for the measurement of wavefront aberration of a human eye, the wavefront from the eye pupil or cornea plane is generally relayed to the wavefront sensing or sampling plane using the well known 4-F relay principle once or multiple times (see for example, J. Liang, et al. (1994) "Objective measurement of the wave aberrations of the human eye with the use of a Hartmann-Shack wave-front sensor," J. Opt. Soc. Am. A 11, 1949-1957; J. J. Widiker, et al. (2006) "High-speed Shack-Hartmann wavefront sensor design with commercial off-the-shelf optics," Applied Optics, 45(2), 383-395; U.S. Pat. No. 7,654,672). Such a 4-F relay system will preserve the phase information of the incident wavefront while allowing it to be relayed without detrimental propagation effects. In addition, by configuring an afocal imaging system using two lenses of different focal lengths to realize the 4-F relay, the relay can allow for the magnification or demagnification of the incident wavefront with an associated demagnification or magnification of the divergence or convergence of the incident wavefront (see for example, J. W. Goodman, *Introduction to Fourier Optics*, $2^{nd}$ ed. McGraw-Hill, 1996).

Figure 1:
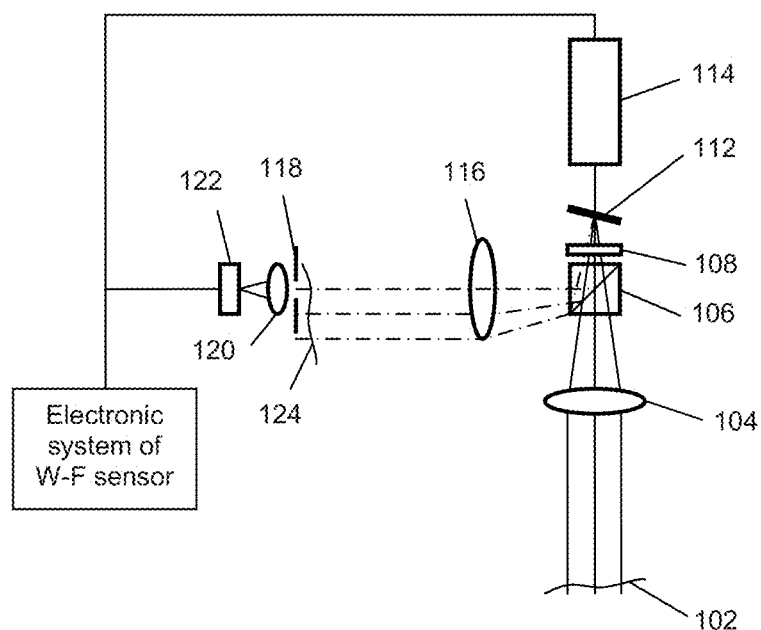
FIG. 1 depicts a sequential wavefront sensor.

FIG. 1 shows an example schematic diagram of an embodiment of a sequential wavefront sensor 100 that utilizes a 4-F relay system. A linearly polarized input beam of light having a wavefront 102 is focused by the first lens 104. The focusing beam travels through a polarization beam splitter (PBS) 106, which is arranged, in such a manner that its pass-through polarization direction is aligned with the polarization direction of the incoming beam. As the result, the linearly polarized convergent beam will pass through the PBS 106. A quarter-wave plate 108 is placed behind the PBS 106 with fast axis oriented so that a circularly polarized beam is emerged after passing through the quarter-wave plate 108.

In the following description the term "wavefront shifting" is used to describe two-dimensional transverse shifting of the wavefront at the final wavefront image plane and the term "wavefront scanning" is used to describe wavefront shifting achieved by using an optical beam scanner or displacer.

The input convergent beam is focused on the reflective surface of a tilted scanning mirror 112, which is mounted on a motor shaft 114. The light beam reflected by the mirror is divergent, with its beam central chief ray changed to a direction that is dependent on the tilting angle of the scan mirror 112 and the rotational position of the motor 114. It is expected that the reflected beam is still circularly polarized, but the circular polarization rotation direction will be changed from left hand to right hand or from right hand to left hand. Hence, upon passing through the quarter-wave plate 108 for a second time on its return path, the beam becomes linearly polarized again, but with its polarization direction rotated to an orthogonal direction with respect to that of the original incoming beam. Therefore, at the polarization beam splitter 106, the returned beam will be mostly reflected to the left as shown by the dashed light rays in FIG. 1.

A second lens 116 is placed on the left next to the PBS 106 to collimate the reflected divergent beam and to produce a replica of the original input wavefront 124. Due to the tilting of the scan mirror, the replicated wavefront 124 is transversely shifted. An aperture 118 is placed behind the second lens 116 and right in front of the sub-wavefront focusing lens 120 to select a small portion of the replicated wavefront 124. The sub-wavefront focusing lens 120 focuses the selected sub-wavefront onto a position sensing device 122, which is used to determine the centroid of the focused light spot generated from the sequentially selected sub-wavefronts. By rotating the motor 114 and changing the tilting angle of the scan mirror 112 in a stepped fashion, the amount of radial and azimuthal shift of the replicated wavefront can be controlled such that any portion of the replicated wavefront can be selected to pass through the aperture 118 in a sequential way. As a result, the overall wavefront of the original incoming beam can be characterized as for the case of a standard Hartmann-Shack wave-front sensor with the exception that the centroid of each sub-wavefront is now obtained in a sequential rather than a parallel manner.

The first and second lenses 104 and 116 of the example depicted in FIG. 1 serve the function of a 4-F relay system. The beam scanner 112 is located at the back focal or Fourier transform plane of the first lens 104 and is also located at the front focal plane of the second lens 116.

However, when a 4-F relay system is used in a sequential wavefront sensor as depicted in FIG. 1, which uses an angular beam scanner at or near the Fourier transform plane for shifting the wavefront, if the absolute diopter value of the original wavefront from the eye is large (either positive or negative), the beam width at the Fourier transform plane can be too large to be completely intercepted by the beam scanner. In order to cover a wide eye diopter range, the beam scanner needs to have a large beam interaction window to ensure that optical energy coming from an eye pupil is not lost. Unfortunately, such a large window size beam scanner is either generally not easily available, or, if commercially available, will be very bulky and expensive if high speed scanning is needed. There is thus a need for an optical design that will allow the use of a relatively low cost and commercially available beam scanner in a sequential wavefront sensor to cover a large eye diopter range.

Figure 2A:
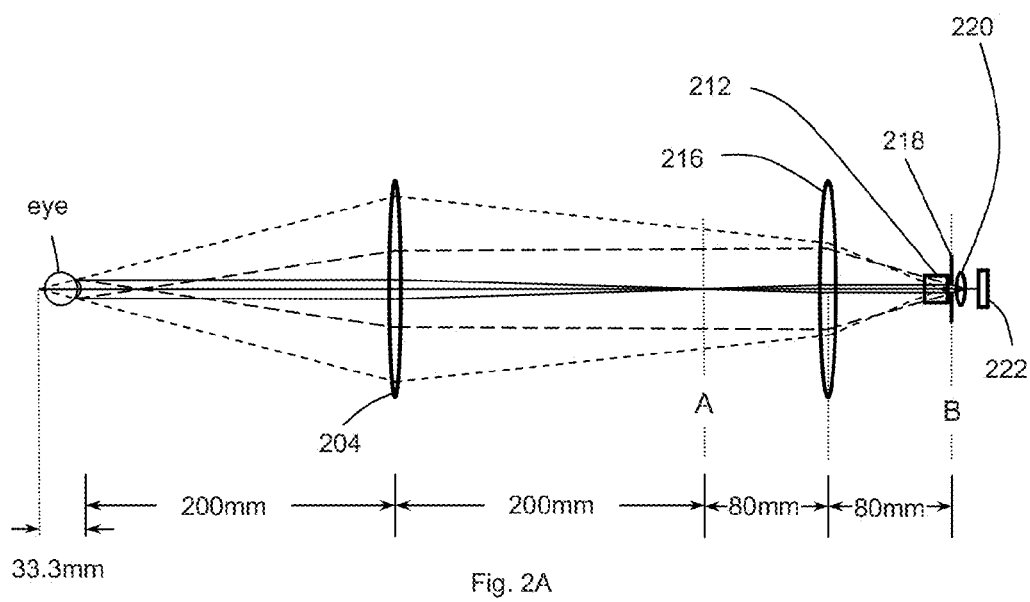
FIG. 2A shows one embodiment in which a single stage 4-F wavefront relay system is combined with a transmissive wavefront shifting device that scans the wavefront transversely to enable only a portion of the shifted wavefront to pass through a wavefront sampling aperture and to be focused onto a position sensing device.

FIG. 2A shows an example embodiment in which a single stage 4-F wavefront relay system is combined with a transmissive wavefront shifting device that scans the wavefront transversely to enable only a portion of the shifted wavefront to pass through a wavefront sampling aperture and to be focused onto a position sensing device. In this embodiment, the light beam path is unfolded. It should be noted that the purpose of unfolding the light path is for an easy explanation of the technical details. In a real device, the light path can be folded in different ways. For example, the light path can be folded or bent to make the device physically compact to facilitate the integration of the wavefront sensor with a slit lamp bio-microscope or a surgical microscope.

In the example of FIG. 2A, the first lens 204 of the 4-F relay system has a diameter of 40 mm and an effective focal length of 200 mm, which is a typical focal length (roughly equal to the working distance) of an ophthalmic surgical microscope. The eye is preferably located at or near the front focal plane of the first lens 204 of the 4-F relay system. The Fourier transform plane A of the 4-F relay system is at the back focal plane of the first lens 204 and the front focal plane of the second lens 216 of the 4-F relay system as shown by the vertical dashed line represented by the capital letter A. In this example, the second lens 216 of the 4-F relay system has a diameter of 40 mm and an effective focal length of 80 mm. The relayed wavefront image plane of the 4-F relay system is at the back focal plane of the second lens 216 as shown by the vertical dashed line represented by the capital letter B. Due to the difference in the effective focal length of the two lenses used in the 4-F relay system, the replica or image of the incident wavefront from the eye is optically de-magnified in the transverse dimension by 200/80=2.5 times, as is well known to those skilled in the art.

As can be seen from FIG. 2A, when the eye is emmetropic and hence the wavefront from the eye is close to being planar, the light beam from the eye is a relatively narrow and parallel beam as represented by the solid light rays. If the eye pupil has a diameter of 5 mm, for example, the beam will be about 5 mm in diameter. The exact beam shape is also dependent on the light scattering spot size on the retina which is a function of the light beam (not shown in FIG. 2A) being delivered to the eye to create the wavefront.

After passing through the first lens 204 of the 4-F relay system, the beam from the eye will be focused on the optical axis at the first Fourier transform plane A where it will transform from a convergent beam to a divergent beam. The beam is re-collimated by the second lens 216 of the 4-F relay system, and the beam diameter will be reduced to 2 mm because of the difference in the effective focal length of the two lenses used in the 4-F relay system. In this emmetropic case, if a beam scanner with a relatively small window were located somewhere at the first Fourier transform plane A, as in the example depicted in FIG. 1, then the beam would be completely intercepted by the beam scanner placed there. Meanwhile, an angular scan at the Fourier transform plane A would be translated into a transverse beam displacement after the second lens 216 of the 4-F relay system as is well known to those skilled in the art.

However, if the eye is aphakic or highly hyperopic or highly myopic, the wavefront from the eye will no longer be planar but very divergent or convergent. In other words, the beam from the eye will no longer be a relatively parallel beam; instead, it will be either a divergent or a convergent beam. The shorter dashed light rays in FIG. 1 shows the case of a divergent wavefront with a diopter value of +30D (we define divergent wavefront from an eye as having positive diopter value and convergent wavefront from an eye as having negative diopter value). +30D represents normal aphakia (with a typical hyperopic diopter value of +20D) plus an additional cornea induced hyperopia of +10D. As can be seen, when the divergent beam represented by the shorter dashed light rays propagates to the Fourier transfer plane A, the beam width is quite large. In fact, if the eye pupil is 5 mm in diameter and the wavefront from the eye has a hyperopic diopter value of +30D, this is equivalent to a divergent beam in free space coming from a point source located at 33.3 mm behind the eye pupil plane or 233.3 mm away from the first lens of the 4-F relay system. This divergent beam is limited by the 5 mm eye pupil at 33.3 mm from the point source location to form a divergent beam cone.

With the given assumptions, it can be found that this beam, when reaching the first lens location of the 4-F relay system, will be 35 mm in diameter and when it reaches the Fourier transform plane A, it will be 30 mm in diameter. So if a beam scanner were to be used at the Fourier transform plane A, as in the example depicted in FIG. 1, to serve the purpose of shifting the wavefront, the required window size would be at least 30 mm in diameter for a 5 mm eye pupil. Such a large window size scanner is not ideal in terms of cost, size, and commercial viability.

The longer dashed light rays in FIG. 2A shows a highly myopic case of −20D, in which a convergent beam from the eye will converge to a point after leaving the eye for a distance of 50 mm and transform to a divergent beam as represented by the longer dashed light rays. Although this −20D beam is narrower than the +30D beam in the Fourier transform space between the two lenses, it is still much wider than the emmetropic beam. These discussions show that the scanning scheme as in the example depicted in FIG. 1 can only function within a limited diopter range that is dependent on the limitation of the light beam interaction window size of the scanner located somewhere near the Fourier transform plane.

In the present disclosure, we propose to arrange the wavefront shifting device such as a beam scanner not in the first Fourier transform space between the first lens and the second lens, but rather either in a wavefront image space or in a following stage Fourier transform space.

Figure 2B:
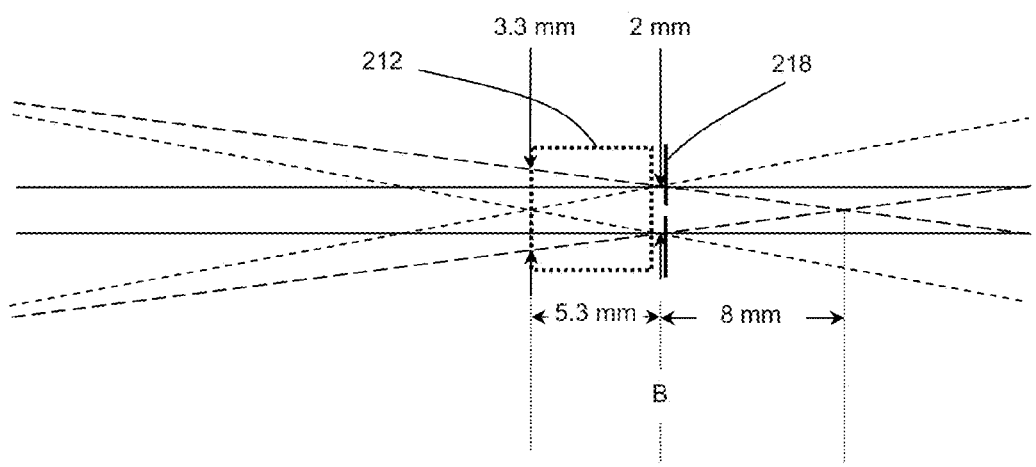
FIG. 2B shows a zoomed-in schematic diagram of the region in the wavefront image space of FIG. 2A that corresponds to an axial range over which the beam is relatively narrow.

As can be seen in FIG. 2B, which is a zoomed-in schematic diagram of the region in the wavefront image space of FIG. 2A that corresponds to an axial range over which the beam is relatively narrow, when both the shorter and longer dashed light ray represented beams reach the wavefront image plane B, they are de-magnified to a beam diameter of 2 mm as in the emmetropia case. However, the shorter dashed light ray represented beam will transform from a highly convergent beam to a highly divergent beam in the wavefront image space before the relayed wavefront image plane B, and the longer dashed light ray represented beam will transform from a relatively highly convergent beam to a relatively highly divergent beam in the wavefront image space after the relayed wavefront image plane B. In other words, the wavefront from the eye pupil is transferred to the wavefront image plane B with the +30D beam being highly divergent at the wavefront image plane B, and the −20D beam being relatively highly convergent at wavefront image plane B.

The optical de-magnification in the transverse dimension of the relayed wavefront is associated with an increase in beam cone divergence (or convergence) as compared to that in the object space. It can be calculated using thin lens image formation formula that for the +30D divergent wavefront from the eye, the relayed point source image is located at 5.33 mm in front of the B plane, while for the −20D convergent wavefront from the eye, the relayed point source image is located at 8.0 mm behind the B plane.

Given that at the object or patient eye side, the +30D beam cone divergence (defined as the ratio of beam width at an axial position over the distance between the point source location and the plane of beam width measurement) was 5 mm/33.33 mm=0.15 and now the relayed beam cone divergence is 2 mm/5.33 mm=0.375, so the beam cone divergence is increased by 0.375/0.15=2.5 times. Similarly, the −20D beam cone convergence was 5 mm/50 mm=0.1 and now it is 2 mm/8 mm=0.25, so the beam cone convergence is also increased by 0.25/0.1=2.5 times.

Therefore, over an eye wavefront diopter range of +30D to −20D for a 5 mm eye pupil, there is an axial range in the wavefront image space over which the beam will be relatively narrow. The question is where to arrange the wavefront shifting device (such as an optical beam scanner) within this axial range such that while the beam can be completely intercepted by the beam scanner, there is also a transverse shift of the relayed wavefront when the scanned beam travels to the wavefront relay plane B.

Note that as the wavefront beam width range is a function of the eye pupil size, the eye wavefront diopter measurement range per a certain beam scanner window size can thus be adjusted by scanning a smaller area across the relayed wavefront. One can therefore take advantage of this property to sample a smaller area over the eye pupil size in order to obtain a different calibration curve and hence to cover an even large eye diopter measurement range.

For a perfect wavefront relay system, at the wavefront relay plane B, the beam width will be 2 mm in diameter. Over the eye diopter range from +30D to −20D for a 5 mm eye pupil, the beam width along the optical axis will vary in the wavefront image space depending on the wavefront diopter value of the eye, but will be confined to within a certain space volume as indicated by the shorter dashed light rays to the right of the wavefront relay plane B, and by the longer dashed light rays to the left of the wavefront relay plane B. In the case as shown in FIGS. 2A and B, the best place for arranging a transmissive optical beam scanner or displacer 212 will be somewhere to the left of the wavefront relay plane B, as long as the scanner window is bigger than the beam width over the whole intended eye diopter range.

For example, if a transmissive optical beam scanner 212 has a beam interaction window of about 4 mm in diameter; it can be arranged to the left of the wavefront relay plane B as shown by the dotted box in FIG. 2B. The transmissive beam scanner 212 can be an electro-optic, magneto-optic, acousto-optic, liquid crystal or mechanical scanner. It should be noted that in general, a transmissive beam scanner is made from an optical material having a refractive index greater than that of air, and accordingly, the wavefront relay plane B will be pushed further to the right, which can be advantageous in terms of transversely shifting the wavefront at the wavefront relay image plane B, if the scanner is an angular scanner.

In other words, in the case of an angular beam scanner, the distance between the front surface of the beam scanner and the wavefront relay plane B will affect the scan angle range required in order to enable the whole wavefront to be sampled. If the beam interaction window of the beam scanner is larger, it can be arranged further to the left to reduce the scan angle range requirement. Alternatively, if the scan angle range per the specification of the scanner falls short of what is desired, an optical design optimization can be performed to select a shorter effective focal length lens for the second lens of the one stage 4-F wavefront relay to ensure that the resultant scan angle range requirement for the beam scanner is within the specification of the device.

It should be noted that with angular beam scan, the wavefront, when relayed to the wavefront image plane B, can suffer a DC angle or wavefront tilt offset as well as some other added aberrations such as astigmatism and/or coma. However, these DC offsets and/or additional inherent aberrations can be taken into consideration through calibration and software data processing so that they can be subtracted from the overall aberrations measured as is well known to those skilled in the art.

Figure 3:
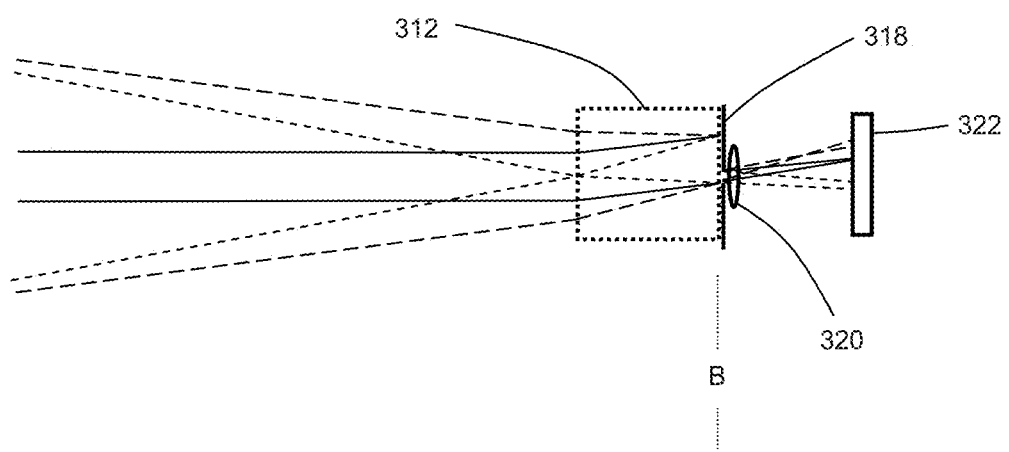
FIG. 3 shows an example case of a transmissive angular beam scanner being used in the wavefront image space as shown in FIGS. 2A and 2B to do the wavefront beam scanning.

FIG. 3 shows an example case of a transmissive angular beam scanner 312 being used to do the scanning. The beam scanner 312 is assumed, in this example, to have an optical medium with a length such that the wavefront image plane B is just at the back exit plane of the scanner medium. As can be seen, when a collimated emmetropic beam from the eye is angularly scanned, as the beam reaches the wavefront image plane B, in addition to the transverse shift of the overall wavefront, there is also a DC offset of the wavefront tilt. As a result, when the emmetropic wavefront is sampled by the wavefront sampling aperture 318 and is further focused by the sub-wavefront focusing lens 320 to land on the position sensing device (PSD) 322 that can be positioned either at the focal plane of the sub-wavefront focusing lens 318 or in front or behind the focal plane, the image spot is not at the axial central position of the PSD 322. Instead, there will be a DC offset as a result of the wavefront tilt.

The image spot positions of the +30D beam and the −20D beam are also shown in FIG. 3 by the shorter and longer dashed lines respectively. They are not well focused at the focal plane as the beams are divergent and convergent before hitting the sub-wavefront focusing lens, and are at positions different from the reference image position of the emmetropic case. However, the image spot can still be used to indicate the image spot centroid position and calibration can be employed to correlate the spot position to the actual wavefront aberration.

It should be pointed out that in this case, if the position sensing device 322 is a 2D (two-dimensional) lateral effect detector or a 2D detector array such as a CCD or CMOS image sensor, the centroid position can be figured out through software based data processing. However, if the position sensing device 322 is a quadrant detector, the image spot may land on only one of the 4 quadrants if the image spot is too small, making it impossible to figure out the centroid position of the image spot. On the other hand, if the image spot is too large, it can fall outside the quadrant detector, making the reading not accurate. In addition, for a convergent or divergent sampled sub-wavefront as compared to a planer sub-wavefront, the image spot size on the quadrant detector can also vary and as a result, different tilt angle can lead to the same ratio of optical energy landing among each of the 4 quadrants.

To overcome these limitations, the axial position and/or focal length of the sub-wavefront focusing lens 320 can be changed or made dynamically variable to ensure that the image spot is made large enough or to a desired size range (for example with a size or diameter about equal to the size of one quadrant) so that the image spot can be shared by the 4 quadrants. Alternatively, the focal length of the sub-wavefront focusing lens 318 can be properly selected and the position of the quadrant detector can also be properly selected to ensure that within the desired eye diopter measurement range, the image spot is always shared by the 4 quadrants and will not move beyond the photosensitive area of the quadrant detector. As another alternative, the position of the quadrant detector can also be made dynamically movable, especially axially to cater for the change in the image spot size of the sample sub-wavefronts. As still another alternative, an axicon lens can be used as the sub-wavefront focusing lens to keep the image spot size within a desired size range. As still another alternative, a diffuser can be arranged in front of the quadrant detector to deliberately diffuse a relatively well focused and small image spot such that after travelling through a certain distance of the diffuser, the image spot will be shared by the 4 quadrants.

Figure 4:
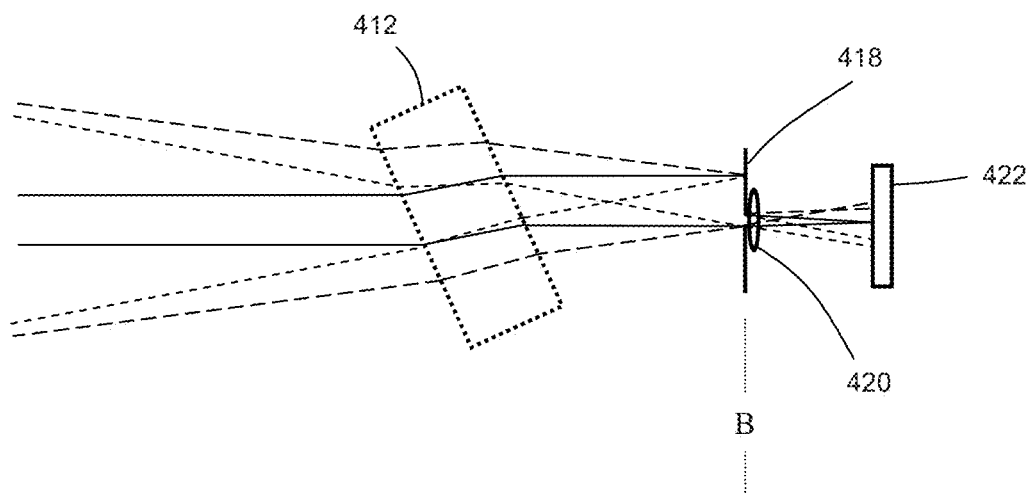
FIG. 4 shows another example of a transmissive beam scanner being used in the wavefront image space as shown in FIGS. 2A and 2B to realize wavefront beam displacement by dropping a tilted glass block into the optical path or by rotating such a glass block around the beam axis.

FIG. 4 shows another example of a transmissive beam scanner 412 realized by dropping a tilted glass block into the optical path or by rotating such a glass block around the beam axis and changing the tilt angle. The scanner 412 is an optical beam displacement scanner. As the glass block has a refractive index higher than that of air, the wavefront image plane B is pushed further to the right. The glass block tilt angle and/or thickness will determine the amount of beam displacement. Again, there can be additional aberrations (such as astigmatism) introduced to the wavefront as a result of beam displacement scanning but these additional aberrations can again be taken into consideration through calibration and software data processing.

Figure 5:
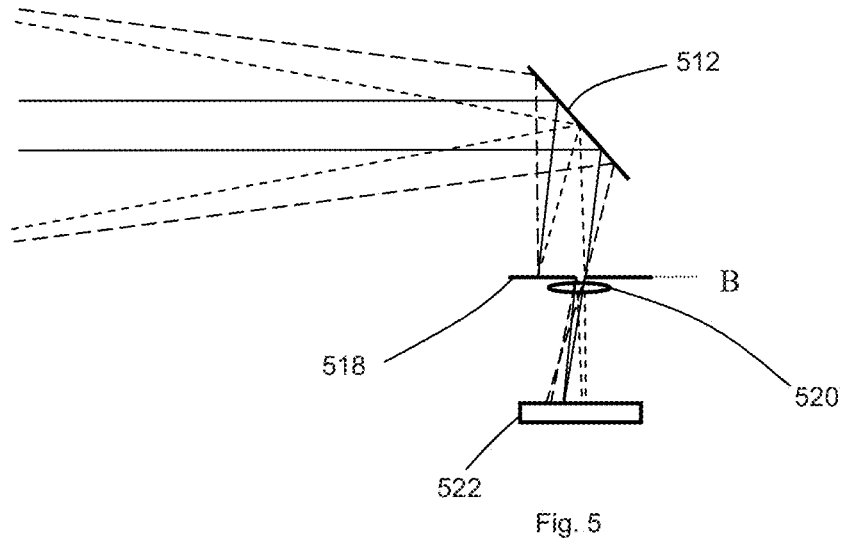
FIG. 5 shows an example of a reflective beam scanner being used in the wavefront image space before the wavefront image plane to reflect the wavefront beam sideway and meanwhile to angularly scan the beam.

FIG. 5 shows an example of a reflective beam scanner 512 being used to reflect the wavefront beam sideway and meanwhile to scan the beam. It should be noted that although in FIG. 5, the wavefront beam is shown to be deflected sideway with the beam turned by about 90 degree relative to the incident beam, this should not be a limitation and the beam can be deflected by any angle. One issue associated with deflecting the beam by about 90 degree is that the beam shape on the reflective scan mirror is generally ellipse-like and this may put a more stringent requirement on the reflective scan mirror shape and/or size. Another issue is that since the angular scanning is only symmetric with respect to the normal of the mirror surface that passes through the pivot point, transverse shifting of the wavefront will not be exactly symmetric and this will effectively put extra burden to either the drive signal for the scan mirror or to the algorithm and data processing software for figuring out the exact wavefront aberration.

Figure 6:
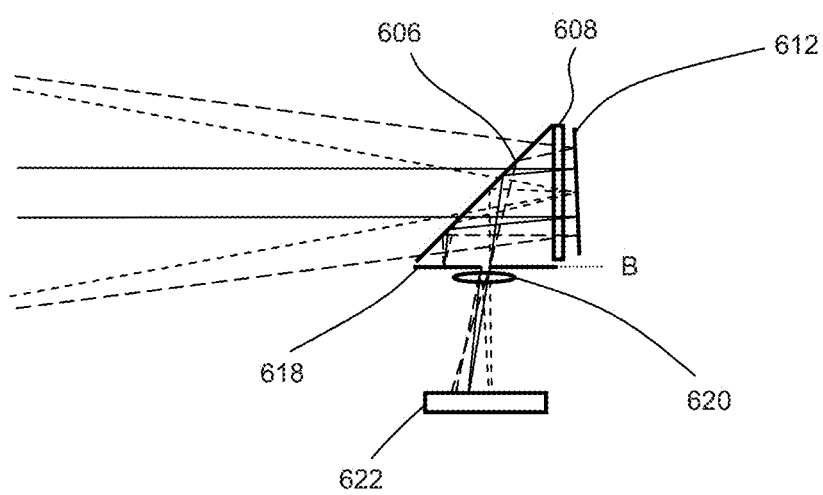
FIG. 6 shows another example of a reflective beam scanner being used in the wavefront image space before the wavefront image plane to reflect the wavefront light beam backward and to more symmetrically scan the beam in terms of transversely shifting the wavefront.

FIG. 6 shows an embodiment that is more symmetric in terms of transversely shifting the wavefront. This embodiment uses an optical beam scanning mirror 612 combined with an optical-energy-efficient reflective configuration, which is in essence a beam folded version of FIG. 3. In this embodiment, the incoming wavefront is assumed linearly p-polarized and a polarization beam splitter (PBS) 606 is combined with a quarter-wave plate 608 or a Faraday rotator to act as an isolator. When the wavefront beam is reflected back by the reflective beam scanner 612 and passes through the wave plate 608 or a Faraday rotator a second time, the polarization direction of the beam will be rotated to an orthogonal direction or to the s-polarization direction, and as a result, the beam will be reflected by the polarization beam splitter 606 sideway or downward to the wavefront sampling aperture 618, from which a sampled sub-wavefront will be focused by the sub-wavefront focusing lens 620 to land on the position sensing detector (PSD) 622. Owing to the need to cover a large eye diopter range, the PBS 606 needs to be functional over a relatively large angle-of-incidence range and a good choice for the PBS 606 can be a wire grid based polarization beam splitter plate designed to operate in the desired near infrared wavelength range, although other specially designed cube or plate PBS can also be used.

At this point, it should be noted that in addition to relaying the wavefront once, one can relay the wavefront twice or multiple times to bring in a number of advantageous wavefront shifting alternatives or opportunities. For example, one can transversely de-magnify the wavefront in an intermediate wavefront relay plane to a small size and position a beam scanner even behind the intermediate wavefront relay plane to still realize the transverse scanning and then to magnify the wavefront through the next wavefront relay stage to the desired wavefront size for sampling.

More importantly, one can select the focal length of the lenses used for the second stage wavefront relay so that for a large eye diopter measurement range, at the second Fourier transform plane the wavefront beam width is small enough to be completely intercepted by an angular wavefront shifting device or beam scanner. As a result, an angular scan at the second or a following Fourier transform plane will lead to wavefront transverse shifting at the final wavefront image plane and the DC wavefront tilt problem will be resolved.

Figure 7:
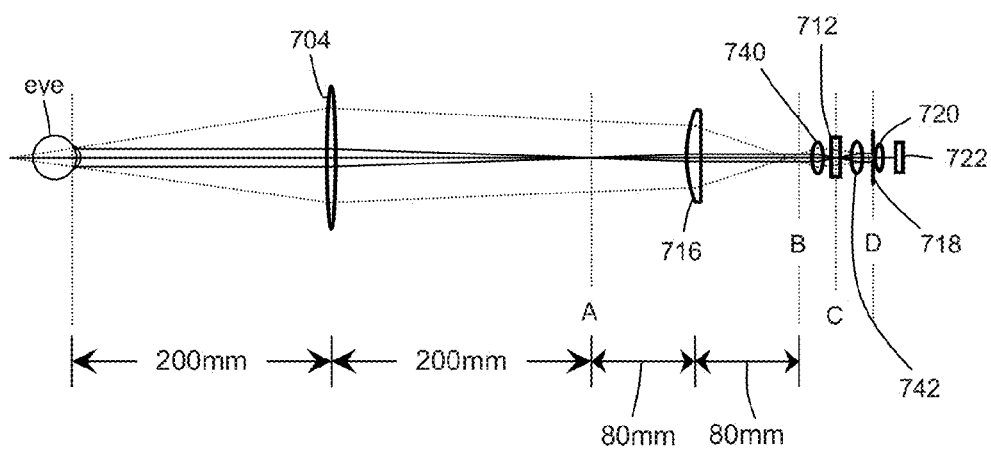
FIG. 7 shows a beam path unfolded embodiment of two cascaded stage 4-F wavefront relays or an 8-F wavefront relay being used in a wavefront sensor module of the present invention.

FIG. 7 shows a beam path unfolded embodiment of two cascaded stage 4-F wavefront relays or an 8-F wavefront relay being used in an example wavefront sensor module. In this embodiment, sequential transverse wavefront shifting is achieved by angularly scanning the wavefront beam at or around the second Fourier transform plane C where the wavefront beam width (over all the desired eye diopter measurement range) is maintained to within a range to be completely intercepted by the beam scanner 712.

Note that the first 4-F wavefront relay stage is the same as that in FIG. 1. In the example of FIG. 7, the second 4-F wavefront relay stage is realized using first and second lenses 740 and 742 of the same focal length of 8 mm and of the same diameter of 8 mm. Note that different focal length lenses for the second stage can be used also as will be shown later. The two cascaded wavefront relay stages are nicely connected in the example of FIG. 7, but this does not mean that precise cascading is absolutely required.

As shown in FIG. 7, after the first wavefront relay at the wavefront image plane B, the wavefront beam width will be reduced 2.5 times, but the beam divergence and/or convergence range will be increased by 2.5 times as discussed before. Due to the use of a short focal length (8 mm) and a relatively large numerical aperture (NA) of the first lens of the second 4-F relay stage, the wavefront beam width at the second Fourier transform plane C is now much smaller than that at the first Fourier transform plane A. A transmissive angular beam scanner 712 can therefore be arranged at the second Fourier transform plane C to completely intercept the wavefront beam. By angularly scanning the wavefront beam at the second Fourier transform plane C, the wavefront image at the second wavefront image plane D will be transversely shifted without any DC wavefront tilt introduced. At the second wavefront image plane D, the transversely shifted wavefront can be sampled by a wavefront sampling aperture 718 and focused by a sub-wavefront focusing lens 720 onto a position sensing device (PSD) 722 as discussed before.

To ensure that the wavefront beam width at the second Fourier transform plane is small, the lens being used as the first lens 740 of the second 4-F relay needs to have a relatively short focal length and a relatively large numerical aperture (NA) or beam cone acceptance angle, as is well know to those skilled in the art.

Figure 8:
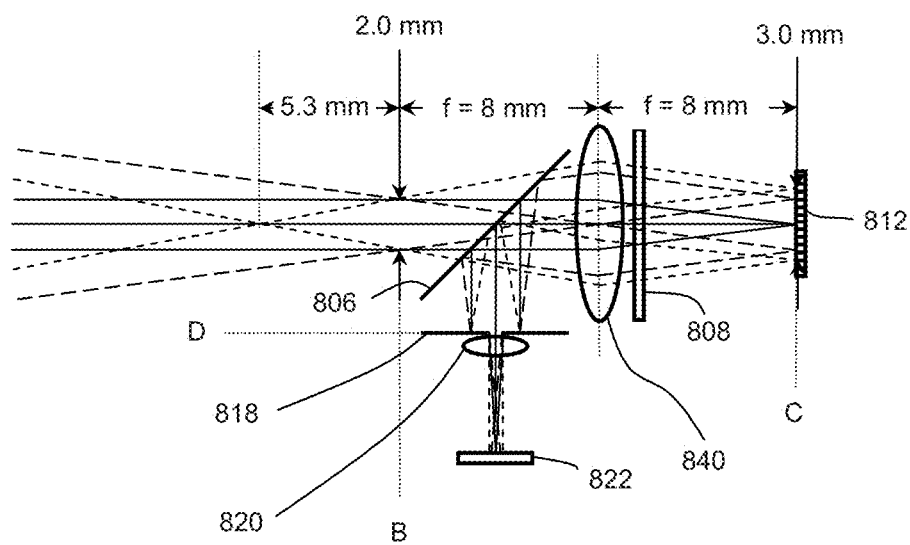
FIG. 8 shows one embodiment of the second stage 4-F wavefront relay of FIG. 7, in which a single lens is used twice and is combined with a reflective beam scanner, a polarization beam splitter (PBS), and a quarter wave plate (¼λ, plate) to realize transverse wavefront shifting at the second wavefront image plane.

FIG. 8 shows one embodiment of the second stage 4-F wavefront relay in which a single lens 840 is used twice and is combined with a reflective beam scanner 812, a polarization beam splitter (PBS) 806, and a quarter wave plate (¼λ plate) 808 to realize transverse wavefront shifting at the second wavefront image plane D. As can be seen in FIG. 8, if the first wavefront image at plane B has a wavefront beam diameter of 2.0 mm, by using a 8 mm focal length lens 840 for the second stage 4-F wavefront relay, it can be found using thin lens formula that for the +30D wavefront beam from the eye, the wavefront beam width at the second Fourier transform plane C is 3.0 mm. In fact, even if the wavefront from the eye is highly myopic with a diopter value of −30D, the beam width at the second Fourier transform plane will still be 3.0 mm simply because the beam width at the second Fourier transform C is directly dependent on the angular distribution of the wavefront tilt at the first wavefront image plane B and for the +30D and −30D wavefront, when they are imaged to the first wavefront image plane B, they have the same angular distribution although one is convergent and the other is divergent. So the design as shown in FIG. 8 will be able to cover an eye diopter measurement range of +30D to −30D.

This 3.0 mm diameter beam at plane C (the second Fourier transform plane) can be reflected by, for example, a MEMS (Micro-Electrical-Mechanical-System) based angular beam scanner 812 and returned to pass through the same 8 mm focal length lens 840 again. Due to the use of the quarter wave plate 808 and the PBS 806, the polarization of the wavefront beam when reaching the PBS 806 on its return path will be rotated by 90 degree to become perpendicular to the original polarization direction and as such, the beam will be deflected sideway (downward in FIG. 8). A wavefront sampling aperture 818 can be placed at the second wavefront image plane D (which could be pushed further away if the PBS is a glass cube) to sample a desired sub-wavefront. The sampled sub-wavefront can pass through a sub-wavefront focusing lens 820 as discussed before to land on a position sensing detector (PSD) 822.

It should be noted that in FIG. 8, the MEMS scanner reflecting surface is shown as being normal to the optical axis of the incident wavefront beam so that only the central portion of the wavefront is sampled by the wavefront sampling aperture 818. Since we are sampling the central portion, for the emmetropic wavefront, the hyperopic wavefront and the myopic wavefront, the average tilt of the sub-wavefront being sampled is normal to the optical axis of the sub-wavefront focusing lens 820 and therefore, the image spot landing on the position sensing detector 822 will be well centered although the image spot size is different for each of the three cases. In other words, the centroid location on the position sensing detector 822 is the same for the three cases when only the central portion of the wavefront from the eye is sampled.

Figure 9:
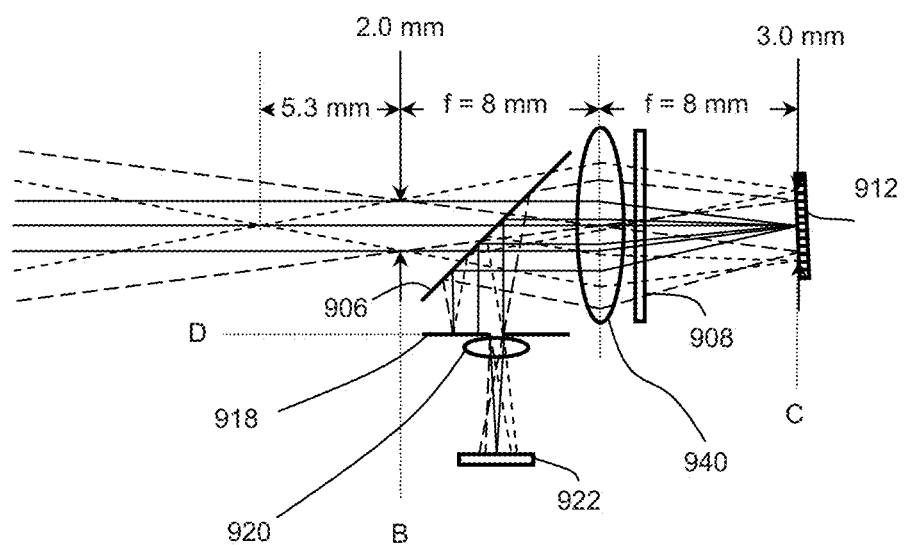
FIG. 9 shows the scanning or angular tilting of the MEMS scan mirror of FIG. 8 and the transverse shift without any DC wavefront tilt offset of the relayed wavefront image at the second wavefront image plane.

The MEMS scanner should be interpreted as being able to scan the incident wavefront beam angularly so that the relayed wavefront image at plane D can be transversely shifted without any DC wavefront tilt offset and FIG. 9 shows such a case. Note that in this case, the emmetropic wavefront sampled by the sampling aperture 918 is still centered relative to the position sensing detector (PSD) 922, but for the hyperopic and myopic wavefront, they are now separated from the center and are on the opposite sides. The end result is basically the same as angularly scanning the wavefront beam at the first Fourier transform plane A using a scanner having a large beam interaction window, which would lead to a transverse shift of the wavefront at the first relayed wavefront image plane B. The difference is that now a scanner with a much smaller beam interaction window can be used.

An issue with the optical configuration of FIGS. 8 and 9 is that the PBS and quarter wave plate can introduce additional undesirable reflections as well as optical energy losses. Furthermore, the PBS needs to have a large angle-of-incidence acceptance range which would mean that most likely a wire-grid type of PBS (which is less optical energy efficient than a standard PBS) should be used. Moreover, the quarter wave plate also most likely needs to be a zero order one in order to cover a broader range of beam incidence angle and also a broader range of the spectral width of the wavefront beam as would be the case of a superluminescent diode (SLD) source.

Figure 10:
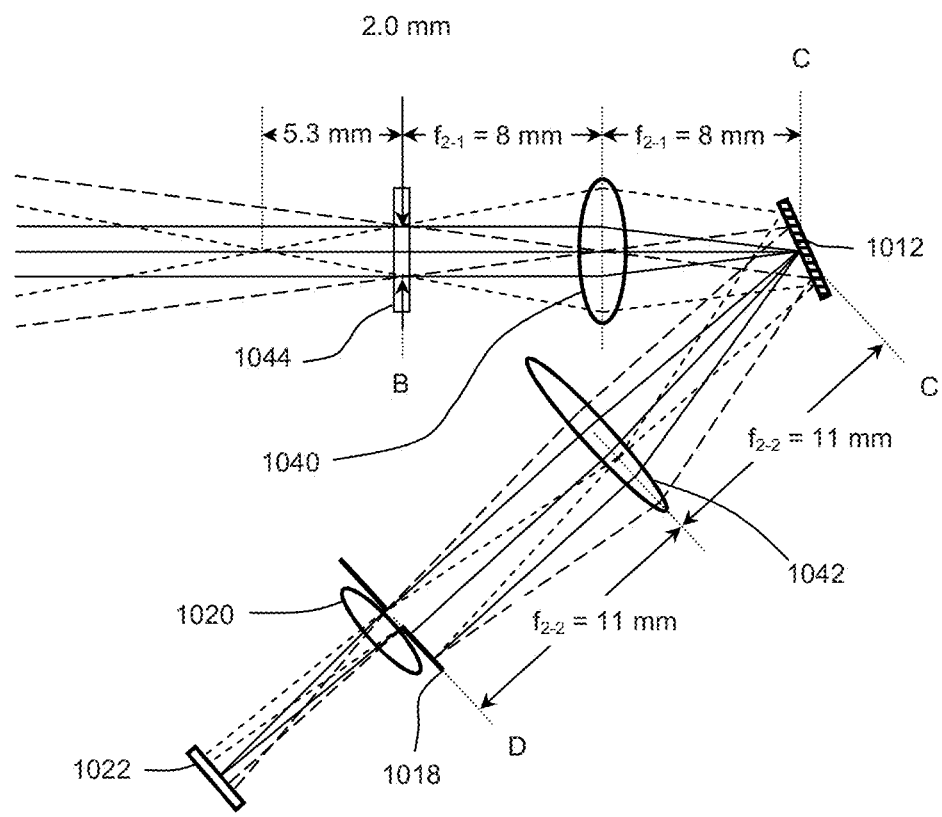
FIG. 10 shows an alternative embodiment of the second 4-F wavefront relay stage of FIG. 7, in which the wavefront beam is reflected and scanned in an oblique sideway manner.

FIG. 10 shows an alternative embodiment of the second 4-F wavefront relay stage. In this embodiment, the wavefront beam is not reflected backward and scanned. Instead, the wavefront beam is reflected and scanned in an oblique sideway manner as long as the reflected wavefront beam does not hit the first lens 1040 of the second 4-F relay. Meanwhile, the angle between the reflected wavefront beam and the incident wavefront beam can be maintained relatively small to reduce the surface area requirement of the MEMS scanner 1012, although another angle such as 45° can be used as well. In addition, the focal length of the second lens 1042 of the second 4-F relay is now larger than the focal length of the first lens 1040 of the second 4-F relay.

This arrangement has a number of advantages. The first one is that compared with FIGS. 8 and 9, the need for a PBS and a quarter wave plate is no longer required and as a result, the issue related to optical energy loss and unwanted reflections is resolved. The first and second lenses 1040 and 1042 being used for the second 4-F relay can be optically antireflection-coated for the relatively narrow spectral range of the SLD source. This will also result in substantial component cost saving. The second advantage is that the focal length of the second lens 1042 of this second 4-F relay can be selected per one's preference to result in a relayed wavefront image with a desired beam width at the second wavefront image relay plane D.

As such, there can exist more optimization opportunities in selecting the focal length of the second lens of the first 4-F relay and the focal length of the first lens of the second 4-F relay 1040 in terms of controlling and/or achieving a desired wavefront beam width range per the eye diopter measurement range and also the alignment and/or assembly precision needed for the manufacturing of the wavefront sensor module. The third advantage is that, by keeping the angle between the reflected wavefront beam and the incident wavefront relatively small, the wavefront beam size as landed on the reflective scanning mirror surface can be maintained small. The fourth advantage is that since angular scanning is done again at the second Fourier transform plane, there will be no wavefront tilt DC offset as discussed before. The fifth advantage as compared to the embodiment of FIGS. 8 and 9 is that the optical elements/components are not positioned too closely to each other and as a result, the mechanical design for mounting them will be a lot easier and less constrained.

As can be seen in FIG. 10, for the three cases of emmetropia, hyperopia and myopia, with the wavefront shifted at the second wavefront image plane D, the sampled wavefront, after being focused onto the position sensing detector 1022 will behave very similarly as in the case of FIG. 9. In other words, the emmetropic wavefront sampled by the sampling aperture is still centered relative to the position sensing detector, but for the hyperopic and myopic wavefront, they are now separated from the center and are on the opposite sides.

One shortcoming of the embodiment of FIG. 10 is that the scanning drive pattern for the MEMS scanner 1012 can be slightly more complicated when compared with the embodiment of FIG. 9. The transverse shift of the wavefront in response to the MEMS mirror scan can be different. When the scan angle range is not large, the response can be approximated by a linear relationship, but an elliptical drive signal instead of a circular scan might be required to result in a circular scan. On the other hand, if the angular scan range is large, the response can be non-linear and there may be a need to make changes to the drive signal in order to end up with a nice circular scan. Alternatively, other scan pattern can be used and software data processing can be employed to extract the wavefront information.

It should be noted that when the wavefront scanning action is performed at the second or a following Fourier transform plane, the wavefront beam width can be made much smaller than that at the first Fourier transform plane. Therefore, in addition to what has been discussed in FIGS. 7 to 10, it is practical to also use other angular beam scanning means as has described before to realize wavefront shifting at the final wavefront image plane. A good example is the use of a small rotating optical wedge at the second Fourier transform plane C to realize annular ring sampling of the wavefront.

At this point, it should be noted that when the approach of two or more wavefront relay stages is taken, the relay stages can be made to be nicely interconnected one after another, or to slightly overlap with each other, or to slightly separate from each other. The system will still work because even if the wavefront is not exactly relayed, calibration can take care of the differences. In addition, with multiple wavefront relay stages, since there are wavefront image plane(s) not being occupied, a variable focal length lens 1044 can also be placed at an intermediate wavefront relay plane to dynamically change the sphero-diopter value of the wavefront to compensate for large DC offset of the sphero diopter value and/or to further improve the diopter measurement dynamic range of the wavefront sensor. Alternatively, relatively small lenses of different focusing powers (both positive and negative) can also be dropped in at one or more wavefront image plane(s) to achieve the sphero diopter compensation or to improve the diopter measurement dynamic range of the wavefront sensor.

It should be pointed out that besides the wavefront shifter or beam scanner, there are preferred selections for the other optical elements as well. For example, we have mentioned that with the wavefront beam from the patient eye being highly divergent or convergent, the beam width is large when the beam hits the first and second lens of the first stage 4-F relay as shown in FIG. 2 and FIG. 7. In this case, if spherical lenses are used as the first and second lens of the of the first stage 4-F relay, spherical aberrations can be introduced by these lenses, especially the second lens as it has a relatively shorter focal length. As one feature of the present disclosure, aspheric lens(es) and/or spherical aberration compensation plate(s) can be used in the optical wavefront relay system so that spherical aberration that would be introduced by the use of spherical lens(es) can be substantially reduced. In particular, if the second lens of the first stage 4-F relay is a plano-convex aspheric lens, its front side that faces the first lens of the first stage 4-F relay is preferably convex while the back side is plano. This is because only when the wavefront beam from the patient eye is highly divergent or convergent; the wavefront beam when reaching the two lenses of the first stage 4-F relay will be wide with peripheral light rays passing through the two lenses that need to be corrected to reduce spherical aberration. On the other hand, when the beam from the patient eye is close to being emmetropic, the beam will be narrow and hence will only interact with the central or paraxial portion of the two lenses which will not produce substantial spherical aberrations. The same argument can also be applied to the second stage.

It should also be noted that the wavefront relay system as shown in FIG. 2 and FIG. 7 can work for a patient eye not positioned exactly at the designed distance. As long as the eye location is within a certain range and is known by, for example, a low coherence interference based measurement and the response of the system output as a function of the eye diopter value is monotonic, one can use a calibrated relationship for the actual eye location to figure out the eye wavefront aberration. In other words, the allowed eye location range should be such that over the intended eye refraction diopter range, the effective wavefront at the designed working distance does not pass any singularity point.

To illustrate this point, let's look at the case in which the patient eye is located at 150 mm from the first lens instead of being at 200 mm, if the patient eye is hyperopic with a diopter value of +20D, then effectively this is equivalent to a point source located at 50 mm behind the pupil plane of the eye, or a point source located at 200 mm from the first lens of the first 4-F relay, which is the object plane of this first lens. As such, this point source will be relayed to the wavefront image plane also as a point source, which can no longer be properly sampled. Passing this singularity point, a divergent eye wavefront (say for example, with a hyperopic diopter value of +25D) will effectively correspond to a point source located within an axial range between the object plane of the first lens of the first 4-F relay and this first lens, which means that the effective wavefront at the designed 200 mm object plane axial position from this first lens is now convergent. This will result in causing the system output to be no longer monotonic. As an alternative to resolving this problem, an additional lens or a combination of lenses can be dropped into the 4-F relay system when the eye distance is found to be outside the eye location limit range to still make the response of the system monotonic over the designed eye diopter range. This approach will also benefit manufacturing as dropping in a lens or lenses into an existing module will be much less costly than designing and making a different module.

It should also be noted that the wavefront sampling aperture does not have to be located exactly at the final wavefront image plane. If there is a slight offset of the axial position of the wavefront sampling aperture, the consequence is that for a divergent or convergent wavefront from the eye, the same sampling aperture size will sample a slightly different spatial size of the eye wavefront as compared to the emmetropic case. If only sphere and cylinder refractive errors of the eye are to be determined, the issue of inconsistency in the spatial sampling size can be resolved by calibration. On the other hand, the sampling aperture can be deliberately made dynamically axially movable to not only ensure that the sampling aperture is at the wavefront image plane when the eye is located at the designed object plane, but also to cater for the situation in which the eye is not located at the designed object plane and to adjust the sampling aperture axial position so that with the same aperture size, the same size sub-wavefront is sampled.

Figure 11:
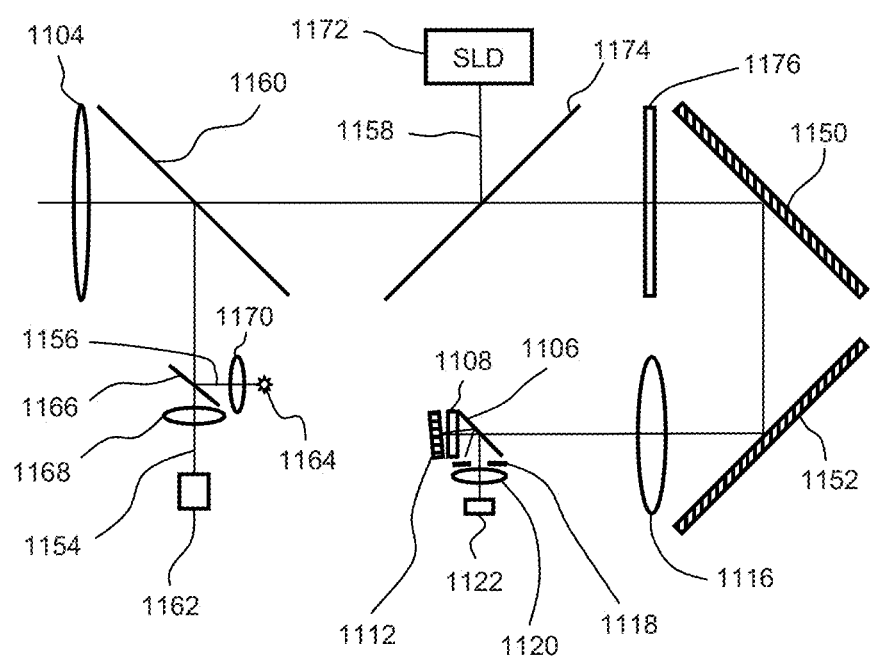
FIG. 11 shows a one stage 4-F relay embodiment of a wavefront sensor module with the wavefront beam path folded. Also shown are one example of the SLD beam launching optics, the eye anterior imaging optics, and the eye fixation optics.

FIG. 11 shows a one stage 4-F relay embodiment with the wavefront beam path folded in a wavefront sensor module. In this embodiment, the wavefront beam path is folded by first and second mirrors 1150 and 1152 (Mirror 1 and Mirror 2) to make the module compact, and a MEMS scan mirror 1112 is combined with a small polarization beam splitter (PBS 2) 1106 and a quarter wave plate 1108 to shift the wavefront as has been discussed per FIG. 6.

It should be noted that by using the MEMS scan mirror 1112 to reflect the wavefront beam backward and scan the beam around the optical axis (rather than to directly deflect the beam sideway and scan beam), the scanning is rotationally symmetric and as a result, when the transversely shifted wavefront is sampled by the wavefront sampling aperture 1118 and focused by the sub-wavefront focusing lens 1120 onto the position sensing detector 1122, the algorithm and data processing software needed to figure out the wavefront aberration, especially the sphere and cylinder diopter values and the cylinder axis, will be extremely simple and fast.

In addition to the folded wavefront beam path, three more beam paths are shown in FIG. 11, a first beam path 1154 for imaging the anterior of the eye, a second beam path 1156 for directing a fixation target to the eye, and a third beam path 1158 for launching a superluminescent diode (SLD) beam to the eye for the creation of the wavefront beam from the eye.

As can be seen in FIG. 11, a dichroic or long-wavelength-pass beam splitter 1160 can be used to reflect at least a portion and more preferably most of visible (and also possibly part of near infrared) light and to substantially or more preferably fully transmit the SLD spectral range near infrared light. The dichroic or long-wavelength-pass beam splitter 1160 should have a large enough light interception window to ensure that the wavefront from the eye over the desired eye diopter measurement range is fully intercepted without being disturbed by the edge of the window. The reflection of the dichroic or long-wavelength-pass beam splitter serves two functions, one is to direct the visible spectral portion of the light from the eye produced by an illumination light source such as that from a surgical microscope or room lighting or other additional illumination lighting to an image sensor 1162 so that a live eye pupil image can be displayed to serve various purposes such as helping a clinician in aligning the eye with respect to the wavefront sensor module. The other function is to direct an image of a visible fixation target 1164 to the eye so that the eye can have a target to fixate if needed.

Figure 12:
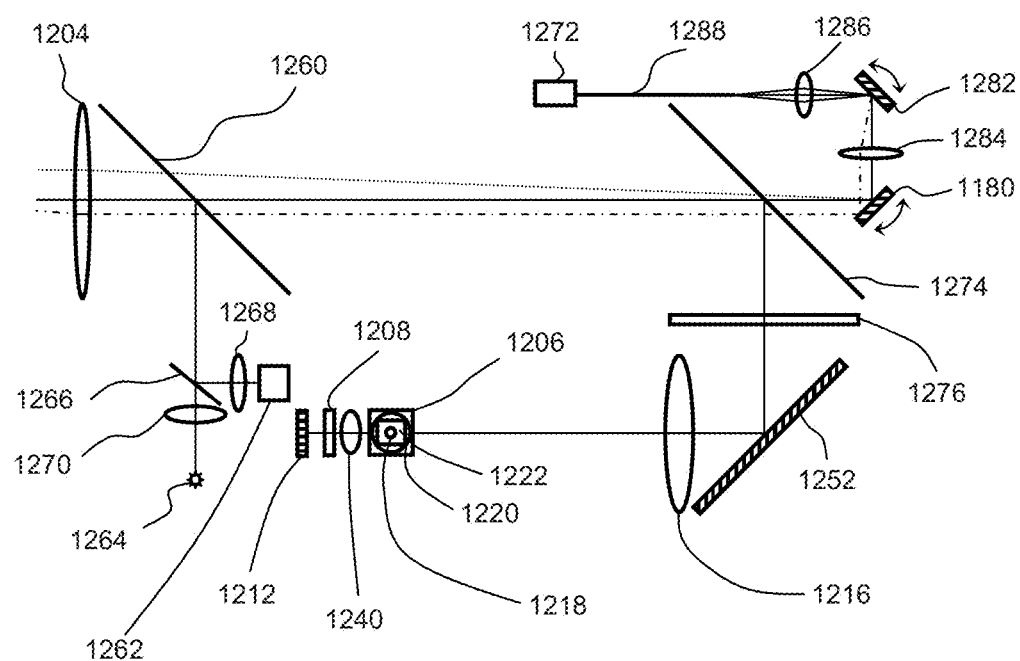
FIG. 12 shows another embodiment of the wavefront sensor module with two 4-F wavefront relay stages. In this embodiment, one mirror used for bending the wavefront beam (Mirror 1) as shown in FIG. 11 is removed and replaced by the large polarization beam splitter (PBS 1) with the SLD beam being launched from behind this PBS. In addition, the SLD beam is scanned or displaced to either follow minor eye movement and/or to land over a small scanned area on the retina.

Further down this reflected light beam path in the wavefront sensor module is a small beam splitter 1166 that serves the function to split/combine the fixation target related light beam and the image sensor related light beam. This small beam splitter 1166 can be of various spectral properties. For example, it can be a simple 50:50 broad band beam splitter designed to operate in the visible spectral range. However, for better optical efficiency, if the fixation light source 1164 has a relatively narrow spectral width, the reflection spectrum of this small beam splitter 1166 can be made to match the fixation source spectrum to allow good reflection of the fixation light and to transmit the rest of the spectrum to the image sensor 1162. But the position of the fixation target 1164 and the image sensor 1162 can be swapped (as shown in FIG. 12) and accordingly, the reflection and transmission spectral property of the small beam splitter 1166 can also be changed.

The lens in front of the image sensor (Lens 1) 1168 can be designed to provide the desired optical magnification for the live image of the anterior of the patient eye on a display (not shown). It can be a dynamic lens used to adjust focus if needed to ensure that the image sensor plane is conjugate with the eye pupil plane so that a clear eye pupil image can be obtained. It can also be a zoom lens so that the clinician/surgeon can use it to change the magnification per his/her desire. The lens in front of the fixation target (Lens 2) 1170 can be designed to provide the patient eye with a comfortable fixation target of the right size and brightness. It can also be used to adjust focus to ensure that the fixation target is conjugate with the retina of the eye, or to fixate the eye at different distances or even to fog the eye per the need of the clinician/surgeon. The fixation light source 1164 can flash or blink or change colors at a rate desired to differentiate it from, for example, the illumination light of a surgical microscope. The color of the fixation light source can also change. The fixation target 1164 can be an image such as a hot air balloon back illuminated by a light source or a micro-display with its displayed patterns or spots variable to the desire of a clinician/surgeon. In addition, the micro-display based fixation target can also be used to guide the patient to gaze at different directions so that a 2D array of eye aberration map can be generated, which can be used to asses the visual acuity of a patient's non-central or peripheral vision.

The fixation target, the eye anterior image, and/or other data could also be transmitted back to the microscope and made visible through the oculars (this is not shown in any of the optical configurations). This information would be projected coaxial with the observer's line of sight by way of the dichroic or beam splitter through a series of lenses or physical distance that would be coplanar to the microscope or biomicroscopes working distance.

The image sensor 1162 can be a black/white or color CMOS/CCD image sensor and the fixation light source can be a red or green light emitting diode (LED) with its output optical power dynamically and/or manually controllable, based on different background lighting conditions. For example, when a relatively strong illumination beam from a surgical microscope is turned on, the brightness of the fixation light source can be increased to enable the patient to easily find the fixation target and fixate on it. A variable diaphragm or aperture (not shown in FIG. 11) can also be arranged in front of or behind the lens 1168 to control the depth of field of the live image of the anterior of the eye. By dynamically changing the aperture size, the degree of blurriness when the eye is axially moved away from the designed distance can be controlled, and the relationship between the blurriness and the eye axial location as a function of the diaphragm or aperture size can be used as a signal to determine the axial distance of the eye. As an alternative, the eye distance can also be measured through well known means such as triangulation using cornea reflected near infrared image spot of two or more near infrared illumination sources, Low coherence interferometry based eye distance measurement as will be disclosed below can also be employed.

In addition to providing a live eye pupil image, the image sensor signal can also be used for other purposes. For example, the live image can be displayed on a heads up display or displayed on a semi-transparent micro-display incorporated in the eye piece of a slit-lamp or surgical microscope.

The live image can be used to detect the size and transverse position of the eye pupil. When it is found that the size of the pupil is small, the wavefront sampling area can be correspondingly reduced. In other words, the pupil size information can be used in a closed loop manner for the automatic and/or dynamic adjustment and/or the scaling of wavefront sensing area per the pupil size or for increasing/decreasing or controlling the dynamic range of the eye diopter measurement.

When it is found that the pupil is not centered well enough, the amount of transverse offset of the eye pupil can be used to compensate for the measured wavefront error that would be introduced by such a pupil position offset. In addition, the SLD beam can be scanned to follow the eye pupil so that the SLD beam will always enter the cornea from the same cornea location as designed to, for example, prevent specularly reflected SLD beam returned by the cornea from entering the wavefront sensor's position sensing device/detector (PSD). The incident SLD beam can be imaged by the image sensor as well for centering of the eye, or intentionally offsetting the SLD beam from the center of the pupil, or for providing feedback/guidance to determine the position of the eye relative to the SLD beam. The wavefront beam shifter/scanner for wavefront sampling can also be tuned with a proper offset to follow the eye pupil movement. Furthermore, when it is found that the eye is being irrigated with water, or there are optical bubbles, or the eye lid is in the optical path, or facial skin, or a surgeon's hand, or a surgical tool or instrument, is in the image sensor's view field and is blocking the wavefront beam path, the wavefront data can be abandoned to exclude the "dark" or "bright" data and at the same time, the SLD 1172 can be turned off.

The image sensor can also be combined with the fixation target and work in tandem to determine the eye distance from the wavefront sensor module. Purkinje images captured by the image sensor can also be used to determine the effective lens position (ELP) based on the principle of reflex. The image sensor can also work with the wavefront sensor in conjunction with refractive wavefront energy shift versus calibration/alignment as an "eye tracker".

Furthermore, the wavefront sensor can be used to figure out if the eye is dry and a reminder in the form of video or audio signal can be sent to the surgeon or clinician to remind him/her when to irrigate the eye. Moreover, the signal from the image sensor can also be used to identify if the patient eye is in a phakic, or aphakic or pseudo-phakic state and accordingly, the SLD pulses can be turned on during only the needed period, or other variables, controls, or metrics can be implemented. These approaches can reduce the patient's overall exposure time to the SLD beam and thus possibly allow higher peak power SLD pulses to be used to increase the wavefront measurement signal to noise ratio, improve feedback metrics, or implement user entry field features through the user interface/display.

In FIG. 11, a large size polarization beam splitter (PBS 1) 1174 is used for launching the superluminescent diode (SLD) beam to the patient eye. The reason for using a large window size is to ensure that the wavefront beam from an eye over the desired large diopter range is not partially intercepted by the PBS, but fully intercepted. In this embodiment, the beam from the SLD 1172 is s-polarized so that the beam is substantially fully reflected by PBS 1174 and is launched to the eye for creating the eye wavefront.

The SLD beam can be pre-shaped or manipulated so that when the beam enters the eye at the cornea plane, it can be either collimated or focused or partially focused (either divergent or convergent) at the cornea plane. When the SLD beam lands on the retina as a small image spot, it will be reflected and/or scattered; or if the beam has a predetermined shape, the geometry or change in geometry of the reflection can be evaluated. As one aspect of the present disclosure, the SLD beam can also be directly used as the fixation target for the patient. The return wavefront beam thus generated will have both the original polarization and an orthogonal polarization. As is well known to those skilled in the art, for ophthalmic wavefront sensor applications, only the orthogonal polarization wavefront beam is usually used for eye wavefront measurement. This is because in the original polarization direction, there can be relatively strong reflected SLD light waves from the cornea and the crystalline/IOL lens, which can introduce significant errors to the wavefront measurement. So another function of the large polarization beam splitter 1174 is to only allow the orthogonally polarized wavefront beam to pass through it and to direct the returned wavefront beam polarized in the original direction sideway to be absorbed or used for other purpose that will be discussed later such as to monitor if there is specular reflection of the SLD by the cornea or eye lens back into the wavefront sensor module.

In FIG. 11, a band pass filter 1176 is arranged after the large polarization beam splitter 1174 to reject any visible light and/or ambient background light, and to only allow the desired relatively narrow spectrum of wavefront beam light that the SLD 1172 generates to enter the rest of the wavefront sensor module.

It should be noted that the dichroic or long-wavelength-pass beam splitter 1160, the large size polarization beam splitter (PBS 1) 1174 and the bandpass filter 1176 can be arranged anywhere along the wavefront beam path. However, by arranging the dichroic or long-wavelength-pass beam splitter before the large size polarization beam splitter (PBS 1), one can avoid imaging onto the live eye pupil image scattered SLD light that can result from reflection of the SLD beam by polarization beam splitter 1174, especially if it is a cube PBS. In addition, by arranging the dichroic or long-wavelength-pass beam splitter 1160, the large size polarization beam splitter 1174 and the bandpass filter 1176 in between the first waveform relay lens 1104 and the second wavefront relay lens 1116, the angle of incidence of the wavefront beam over the desired eye diopter range will be within a smaller range such that all these optical components can function better with standard coating to provide desired performance.

There can be variations to the optical configuration of the wavefront sensor module. In FIG. 11, we showed that the SLD beam is stationary. However, the SLD beam can also be scanned to provide additional advantages. FIG. 12 shows another embodiment of the wavefront sensor module with two 4-F wavefront relay stages. Note that in this embodiment, one mirror used for bending the wavefront beam (Mirror 1, i.e. 1150) as shown in FIG. 11 is removed and replaced by the large polarization beam splitter (PBS 1) 1274 with the SLD beam being launched from behind this PBS 1274. In addition, the SLD beam is scanned to either follow minor eye movement and/or to land on different position of the cornea and/or to land over a small scanned area on the retina. Note also that the narrow band pass filter 1276 is now arranged between the larger polarization beam splitter (PBS 1) 1274 and the next beam folding mirror (Mirror 2) 1252. It should be noted that any of the second stage 4-F wavefront relay as discussed in FIGS. 7, 8, 9, and 10 can be employed in FIG. 12 although only one is shown.

As shown in FIG. 12, since the SLD beam is launched from behind the larger polarization beam splitter (PBS 1) 1274, the launched SLD beam propagating to the eye is p-polarized with respect to PBS 1274; as a result, the wavefront beam with the orthogonal polarization for eye wavefront measurement is s-polarized with respect to PBS 1274 and this beam will be reflected by the larger polarization beam splitter (PBS 1) 1274. Accordingly, there needs to be a corresponding change in the orientation and/or position of the small polarization beam splitter (PBS 2) 1206, the associated quarter wave plate 1208, the wavefront sampling aperture 1218, the sub-wavefront focusing lens 1220 and the position sensing detector (PSD) 1222 as shown in FIG. 12.

In one example of operation, to ensure that the SLD beam always enters the eye at a desired cornea location and is not blocked partially or fully by the iris as a result of eye movement (within a certain eye movement range), a cornea scan mirror 1180 for scanning the SLD beam as shown in FIG. 12 can be positioned at the back focal plane of the first lens of the first 4-F relay 1204 so that the scanner position is conjugate to the retina of an emmetropic eye. In this case, an angular scan of the cornea scan mirror 1280 will cause a transverse scan of the SLD beam with respect to the cornea but still allow the SLD beam to land on the same retina location. The image sensor captured live image of the eye pupil can be used to figure out the transverse position of the eye pupil and to provide a feed back signal to drive the cornea scan mirror 1280 to enable the SLD beam to follow the eye movement.

In another example of operation, to enable the SLD beam to land and also scan around a small area on the retina, a retina scan mirror 1282 as shown in FIG. 12 can be positioned conjugate to the cornea plane at the back focal plane of a SLD beam shape manipulation lens (Lens 3) 1284. Another lens 1286 (Lens 4), can be used to focus or collimate or shape the SLD beam from the output port of, for example, a single mode optical fiber (such as a polarization maintaining (PM) single mode fiber) 1288 onto the retina scan mirror 1282. This lens (Lens 4) 1286 can also be a dynamically focusable or axially movable lens to realize a dynamic control of the SLD beam spot size on the cornea or retina per the eye condition (for example, phakia, aphakia, and pseudo-phakia).

The scanning of the SLD beam over a small area on the retina can provide several benefits. One is to reduce speckle effects resulting from having the SLD beam always landing on the same retina spot area, especially if the spot size is very small. Another benefit is to divert the optical energy over a slightly larger retinal area so that a higher peak power pulsed SLD beam can be launched to the eye to increase the signal to noise ratio for optical wavefront measurement. Still another benefit is to enable the wavefront measurement to be averaged over a small but relatively the same retinal area so that wavefront measurement errors resulting from retinal topographical non-uniformity can be averaged out. Still another benefit is to determine retinal non-uniformity by, for example, measuring the wavefront response as the SLD beam is scanned on the retina.

It should be noted that the scanning of the SLD beam relative to the cornea and the retina can be performed independently but simultaneously. In other words, the two SLD beam scanners can be activated independent of each other but at the same time, synchronously or asynchronously.

In addition, it should be noted that a therapeutic laser beam (not shown In FIG. 12) can be combined as an eye surgery light source with the SLD beam and delivered to the eye through the same optical fiber or through another free space light beam combiner and be delivered to the same scanner(s) for the SLD beam or other scanners so that the eye surgery laser beam can be scanned for performing refractive or retina surgery of the eye. The SLD beam and the eye surgery laser beam can have different wavelength and be combined using optical fiber based wavelength division multiplexing couplers or free space dichroic combiners. The same laser beam or a different laser beam with a visible wavelength can also be used to "mark" the eye or "guide" the surgeon, i.e. "overlaying" on the eye so that the surgeon can see the laser mark(s) through the surgical microscope.

Figure 13:
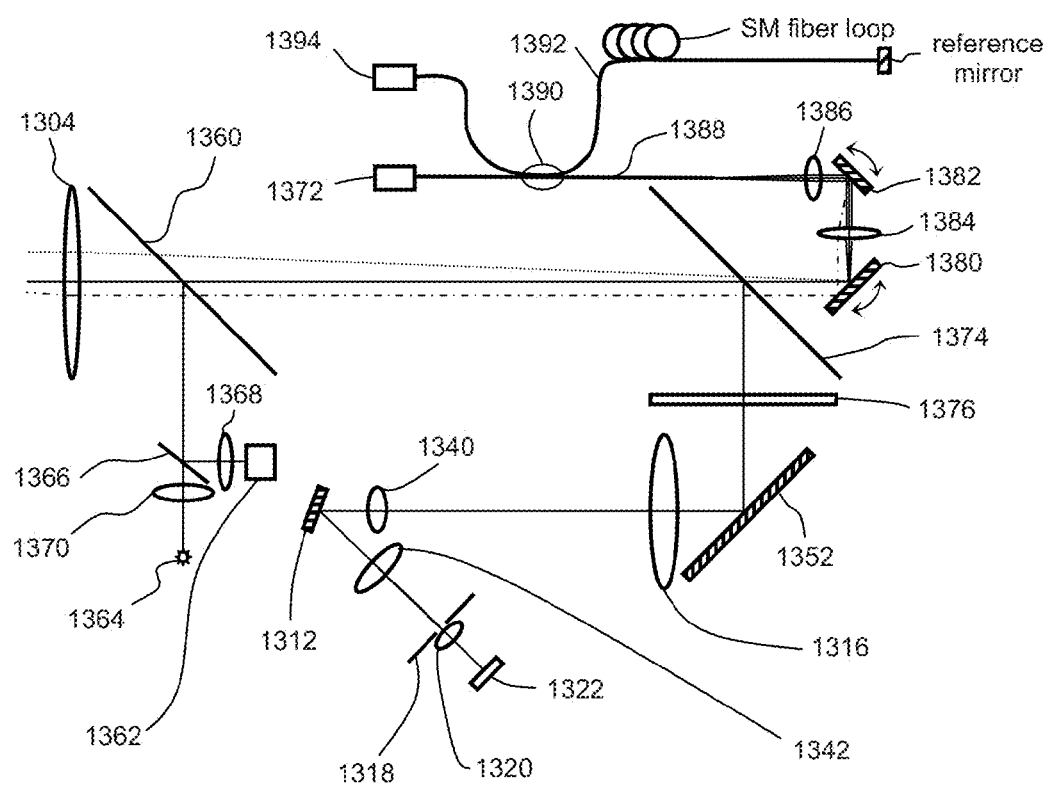
FIG. 13 shows another two 4-F wavefront relay stage embodiment, in which the eye returned light waves with the original polarization as compared to the launched SLD beam are used for the measurement of eye distance from the wavefront sensor module, the location of the eye lens (either natural or implanted) in the eye, the anterior chamber depth, the eye length, and potentially other eye anatomic parameters such as cornea and/or lens curvature of both the front and back surfaces.

Although for eye wavefront measurement, only the beam returned from the retina with an orthogonal polarization is used, this does not mean that those returned beams from the cornea, the eye crystalline lens (or IOL) and the retina with the original polarization are useless. On the contrary, these returned beams with the original polarization can provide very useful information. FIG. 13 shows another two 4-F wavefront relay stage embodiment, in which the second 4-F relay stage is similar to what we have discussed in FIG. 10. Note that in FIG. 13, the eye returned light waves with the original polarization are used for the measurement of eye distance from the wavefront sensor module, the location of the eye lens (either natural or implanted) in the eye, the anterior chamber depth, the eye length, and potentially other eye anatomic parameters.

As can be seen in FIG. 13, the returned light waves that pass through the larger polarization beam splitter (PBS 1) 1374 are collected with a low coherence fiber optic interferometer configuration as is typically employed for optical low coherence (OLC) or optical coherence tomography (OCT) measurements. The SLD output fiber 1388 can be single mode (SM) (and polarization maintaining (PM) if needed) and can be connected to a normal single mode (SM) fiber (or a PM-SM optical fiber if needed) coupler 1390 so that a portion of SLD light is sent to the wavefront sensor module and another portion of the SLD light is sent to a reference arm 1392. The optical path length of the reference arm 1392 can be scanned or changed or even switched to roughly match those corresponding to optical path length of the light returned from one or more optical interfaces of the eye. The light wave returned from different parts of the eye will recombine with the reference light wave returned through the reference fiber arm 1392 at the fiber coupler 1390 to result in optical low coherence interference. This interference signal can be detected by the detection module 1394 as shown in FIG. 13.

Various OLC/OCT configurations and detection schemes, including spectral domain, swept source, time domain, balanced detection and others, can be employed. In order to keep the wavefront sensor module (to be attached, for example, to a surgical microscope or a slit lamp bio-microscope) compact, the detection module, the reference arm (including the fiber loop and the reference mirror that may be axially scanned or moved), and even the SLD and the fiber coupler, can be located outside the wavefront sensor module housing. The reason for doing this is that the detection module and/or the reference arm and/or the SLD source can be bulky depending on the scheme used for the OLC/OCT operation. For example, when a balanced detection scheme is employed as discussed in U.S. Pat. No. 7,815,310, a fiber optic circulator may need to be incorporated in the SLD fiber arm. When time domain detection is employed, the reference arm may need to include an optical path length scanner or a rapid scanning optical delay line. When spectral domain detection scheme is employed, the detection module may need to include an optical spectrometer and a line scan camera. When swept source detection scheme is employed, the SLD source may need to include a wavelength scanner.

In one example of operation, in order to ensure that a relatively strong OLC/OCT signal can be collected, the cornea scan mirror and/or retina scan mirror can be controlled to specifically let relatively strong specular reflections from, for example, the cornea, the eye lens (natural or artificial) and the retina, to return to the optic fiber interferometer so that axial distance of the optical interfaces of these eye components can be measured. This operation can be sequentially separated from the eye wavefront measurement, as in the latter case specular reflection should be avoided. Alternatively, two different wavelength bands can be used and spectral separation/combination can be employed. On the other hand, the OLC/OCT signal strength can be used as an indication on whether specular reflection is being collected by the wavefront sensor module and if yes, the wavefront sensor data can be abandoned.

In another example of operation, the SLD beam can be scanned across the anterior segment of the eye or across a certain volume of the retina and anatomic structure measurement of the various parts of the eye can be made. In particular, the SLD beam can be made to land as a small number of scan points at the center and around one or more annular ring(s) (or other patterns, such as radial, spiral, star) of the cornea to enable the determination or measurement of the cornea refractive power and/or the lens (natural or artificial) refractive power.

At this point, it should be noted that the beam scanners used for shifting the wavefront and for scanning the SLD beam can also have a dynamic DC offset to bring additional benefits to the present disclosure. As one aspect of the invention, the scanner used for shifting and/or scanning the wavefront can be used to provide compensation to potential misalignment of the optical elements as a result of environmental changes such as temperature or mechanical vibration to make the scanned wavefront beam still rotationally symmetric with respect to the wavefront sampling aperture.

Meanwhile, the reference point on the position sensing detector (PSD) can also be adjusted if needed per the compensated image spots locations through calibration. If there is any angular DC offset of the sampled image spot beams relative to the position sensing device/detector (PSD), this can be taken care of through calibration and data processing.

We mentioned that the scanner used for scanning the SLD beam can be employed to follow the eye pupil movement within a certain range through a feedback signal from the image sensor. With the eye moved relative to the wavefront sensor module, even though the SLD beam can be made to enter the eye through the same cornea location at the same angle as it would when the eye is centered well relative to the wavefront sensor module, the returned wavefront beam from the eye will be transversely displaced relative to the optical axis of the wavefront sensor module. As a result, the relayed wavefront will also be transversely displaced. In this case, the DC offset of the scanner used for shifting the wavefront can be employed to compensate for this displacement and still make the scanned wavefront beam rotationally symmetric with respect to the wavefront sampling aperture. In this case, there may be an angular DC offset of the sampled image spot beams relative to the position sensing device/detector (PSD) per the eye pupil transverse position, and again, this can be taken care of through calibration and data processing.

With the combination of information provided by the image sensor, the wavefront sensor, the specular reflection detector and/or the low coherence interferometer, it is possible to combine all the information to realize an auto selection of the correct calibration curve and/or the data processing algorithm. Meanwhile, a data integrity indicator, or a confidence indicator, or a cataract opacity degree indicator, or an indicator for the presence of optical bubbles can be shown to the surgeon or clinician through audio or video or other means. The combined information can also be used for intraocular pressure (IOP) detection, measurement and/or calibration. The combined information can also be used to detect and/or confirm the centering and/or tilt of an implanted intraocular lens (IOL) such as a multi-focal lens. The combined information can also be used for the detection of the eye status, including phakia, aphakia and pseudo-phakia. The wavefront sensor signal can be combined with the OLC/OCT signal to indicate the degree of optical scattering and/or opacity of the eye lens or the optical media of the ocular system.

Again, a laser as an eye surgery light source (not shown In FIG. 13) can be combined with the SLD and delivered to the eye through the same optical fiber or through another free space light beam combiner and the same scanner(s) for the SLD beam or other scanners so that the eye surgery laser beam can be scanned for performing refractive and/or retina surgery of the eye as well as for fine tuning the IOL power of a light adjustable lens or for performing or fine tuning T-cuts as can be done with a femto-second laser, or postoperatively at a slit-lamp biomicroscope using incision techniques LRI/AK, or laser. The same laser beam or a different laser with a visible wavelength can also be used to "mark" the eye or "guide" the surgeon, i.e. "overlaying" on the eye or an eye image so that the surgeon can see the laser mark(s) on a display screen or through the surgical microscope.

At this point, we can state that in the present disclosure, a large diopter range sequential wavefront sensor especially suitable for vision correction procedures has been disclosed. It comprises an optical wavefront relay system that can include one or two or more wavefront relay stage(s), a wavefront sampling aperture positioned at or near the final wavefront relay image plane, a sub-wavefront focusing lens before or after the aperture, an image spot position sensing device positioned behind the sub-wavefront focusing lens, and a wavefront shifting device (such as an optical beam scanner) arranged somewhere either in a wavefront image space or in a Fourier transform space for shifting the wavefront transversely at the final wavefront image plane. One aspect of the present disclosure is that the wavefront shifting device is selected and position to ensure that over a large diopter range of the incident wavefront, the wavefront beam will be fully intercepted by the wavefront shifting device. Preferably, the relayed wavefront beam is de-magnified in the transverse dimension at the wavefront shifting device region so that over a certain axial distance range in the wavefront shifting device space, the wavefront beam width can be maintained relatively small (even with the incident wavefront from the eye being varied over a large diopter range) for the beam to be completely shifted by, for example, a compact beam scanner.

It should, however, be noted that the wavefront relay system should not be limited to the well known 4-F wavefront relay configuration. It can be any optical configuration as long as it serves the function of relaying an optical wavefront from an object plane to an image plane. For example, the wavefront relay configuration disclosed in US20100208203, which comprises three lenses with a negative lens positioned in between two positive lenses, can be used in the present invention once or multiple times.

The wavefront beam does not have to be de-magnified in the wavefront shifting device space. It can be a 1:1 ratio wavefront relay system or even a magnifying wavefront relay system.

The wavefront shifting device space should be interpreted as the volume where the wavefront shifting device is positioned, which can be a wavefront image space or a Fourier transform space. The wavefront shifting device should be interpreted as any device that can perform the function of effectively shifting the wavefront in a sequential manner, including all types of optical beam scanners and displacers. The wavefront shifting device can be arranged in a wavefront image space of one or more wavefront relay stage(s) or in a Fourier transform space of one or more wavefront relay stage(s) as long as it can effectively cause the wavefront to be transversely shifted. The key is to make sure that the wavefront beam over the desired diopter range can be completed intercepted by the wavefront shifting device. Note that wavefront shifting can be achieved by either changing the beam propagation direction or displacing the beam transversely, or through a combined effect or through other means such gradually bending the wavefront beam. The beam scanner can be either transmissive or reflective in nature and the beam scanner can be a light beam angular scanner or a light beam transverse displacement scanner or a combination.

The wavefront sampling aperture can have a fixed aperture size or be a variable aperture with its size and shape adjustable, for example from 0 mm to 6 mm, and can also be dynamically movable axially or transversely if needed. The aperture can also be a drop-in aperture of different sizes, shapes or diameters. The aperture does not have to be in arranged in front of the sub-wavefront focusing lens and can be arranged anywhere after the wavefront shifting device as long as it can serve the function of sampling the wavefront.

The sub-wavefront focusing lens is not absolutely required and can be optional. It can be a lens with a variable focus (or focal length) and can even be a dynamic drop-in lens of different focal length per the state of the eye (such as phakic, aphakic or pseudo-phakic). It does not need to be place right next to the aperture and can be placed far away from the aperture either in front of or after the aperture to, for example, relay the wavefront at sampled at the aperture to a plane in space before or after the position sensing device/detector (PSD). It should be pointed out here that without the sub-wavefront focusing lens, the system can still work as in the case of a Hartmann wavefront sensor versus a Hartmann Shack wavefront sensor. If needed, the focus of the sub-wavefront focusing lens can be made dynamically variable and in doing so, one can adjust its focal length in real time according to the size of the wavefront sampling aperture such that the image spot landing on a position sensing device/detector can be controlled to a desired size for higher precision measurement of the incident wavefront.

The PSD can be a quadrant detector, a lateral effect position sensing detector, a two dimensional detector array, two orthogonal linear detector arrays, or any device that can sense the position of a light beam.

Noted that the optical configurations and related parameters discussed in the above-mentioned embodiments are only examples. In reality, when the wavefront sensor module is to be integrated with a surgical microscope or a slit lamp bio-microscope, the optical configuration and the folding of the optical beam paths can be different based on the consideration of different factors.

Figure 14:
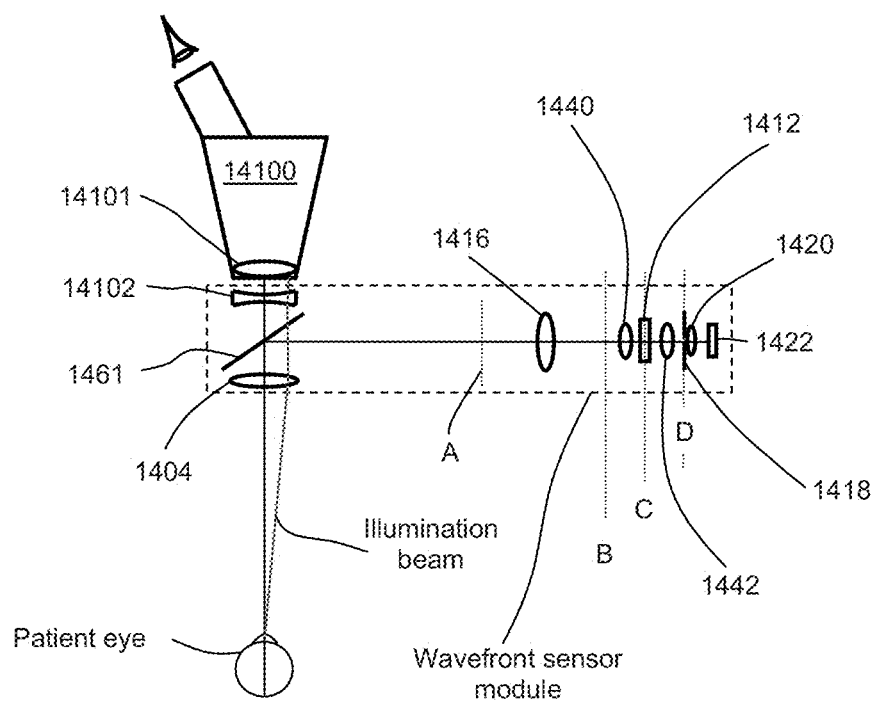
FIG. 14 shows one embodiment of the integration of the presently disclosed wavefront sensor module with a slit lamp or surgical microscope, in which the $1^{st}$ lens of the first 4-F relay is arranged at the very first optical input port of the wavefront sensor module and is shared with the microscope.

FIG. 14 shows one embodiment of the integration of the presently disclosed wavefront sensor module with a surgical microscope 14100. In this embodiment, the first lens 1404 of the first 4-F relay is arranged at the very first optical input port of the wavefront sensor module. This first lens 1404 is shared by a surgical microscope 14100 (or a slit lamp bio-microscope) and the wavefront sensor module. The benefit of arranging this first lens 1404 of the first 4-F relay as close as possible to the patient eye is that the designed focal length of this first lens 1404 can be the shortest per the requirement of a 4-F wavefront relay and accordingly the overall optical path length can be made the shortest. This combined with further folding of the wavefront beam path can make the wavefront sensor module compact. In addition, a larger diopter range of the wavefront from the eye can be covered when compared to a lens of the same diameter but arranged further down stream of the wavefront beam optical path. Furthermore, since there is always a need for the wavefront sensor to have an optical window at this location, this first lens 1404 therefore can serve the dual purpose of both the window and the first lens of the first wavefront relay stage.

The dichroic or short pass beam splitter 1461 as shown in FIG. 14 is used to deflect with high efficiency the near infrared wavefront beam to the rest of the wavefront sensor module while allowing most of the visible light to pass through to the surgical microscope. The dichroic or short pass beam splitter 1461 can be designed to also allow a small portion of the visible light from the eye (or even a larger portion of near infrared light outside the SLD spectrum range if there is such a portion) to be deflected to the wavefront sensor module so that a clear live image of the anterior of the patient eye can be captured by the image sensor as discussed before. It should be noted that the rest of the wavefront sensor module as shown in FIG. 14 is only one representation of a variety of potential optical configurations that can possibly be used. So the interpretation of the wavefront sensor module should cover all possible configurations discussed before.

The compensating lens 14102 above the dichroic or short pass beam splitter 1461 is used to fulfill several functions. Firstly, to ensure that the surgical view to be formed and presented to the surgeon by the surgical microscope is not affected because of the use of the first lens 1404 of first 4-F relay, this compensating lens 14102 needs to be designed to compensate the effect of the shared lens (first lens of first 4-F relay 1404). Secondly, the compensating lens 14102 can also serve as the upper optical window which may be needed to keep dust or moisture from getting into the wavefront sensor module. The third function of the compensating lens 14102 is to direct the illumination beam from the surgical microscope 14100 away from the optical axis so that when the illumination beam hits the shared lens (first lens of first 4-F relay 1404), specular reflections from the shared lens are not directed back into the two stereoscopic view of surgical microscope to interfere with the surgeon's viewing of the surgical scene. Finally, the compensating lens 14102 can also be coated to only allow the visible spectrum of light to transmit through. In this manner, the UV or near infrared spectral portion of illumination light that corresponds to the SLD spectrum from the illumination source will not land on the eye to create any eye returned near infrared background light that can enter the wavefront sensor module to either saturate the position sensing device/detector or to create background noise.

Figure 15:
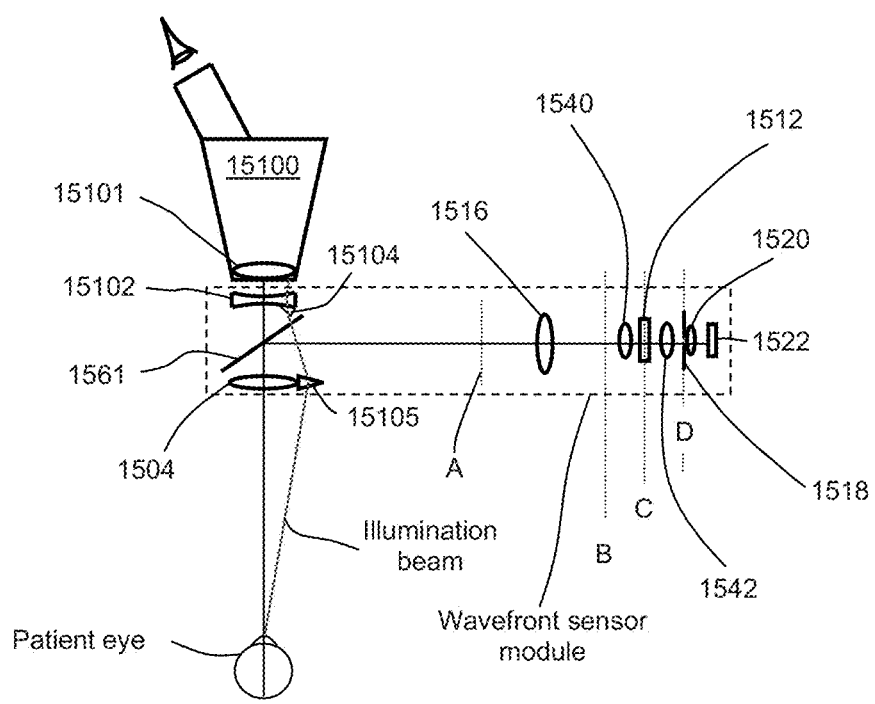
FIG. 15 shows another embodiment similar to FIG. 14 but with additional prisms added to the shared lens and the compensating lens so that the illumination beam from the surgical microscope can be directed to still land on the patient eye but not to create glares in the microscopic view.

Note that the compensating lens 14102 can be specially designed or prism/mirror 15104 can be added so that the portion of the compensating lens right under the illumination beam exit port of the surgical microscope can bend the illumination beam even more and another prism 15105 or mirror can be added next to the bottom lens to re-direct the illumination beam back onto the patient eye as shown in FIG. 15.

Figure 16:
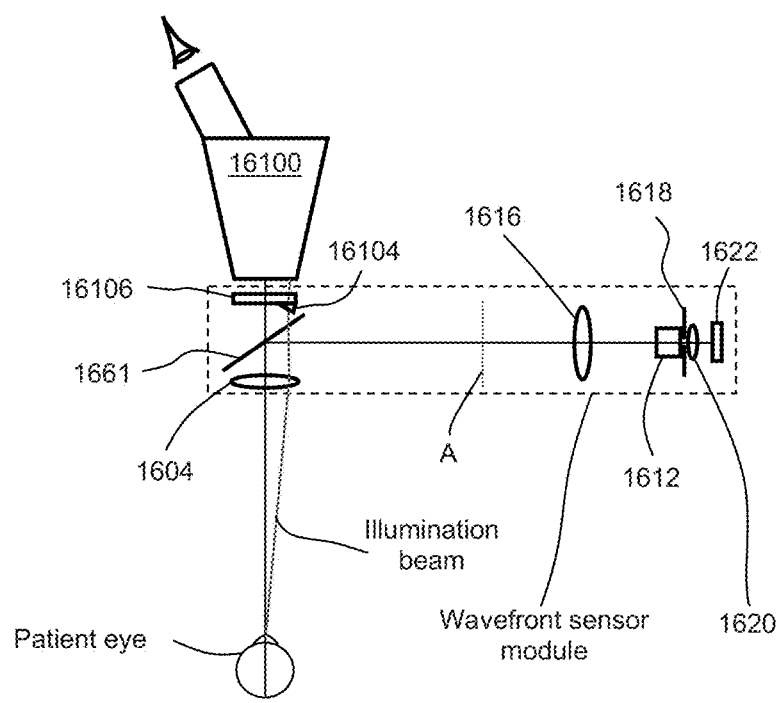
FIG. 16 shows another embodiment of wavefront integration with a microscope in which the objective lens of the microscope is removed and its focusing function is partially or fully served by the shared lens at the input port of the wavefront sensor module.

It should be noted that in the embodiment shown in FIG. 14 and FIG. 15, the original objective lens 14101 or 15101 of the surgical microscope is maintained and not removed. However, as an alternative, the objective lens 14101 or 15101 of the surgical microscope can be removed and its focusing function can be partially or fully served by the shared lens 1604 at the input port of the wavefront sensor module as shown in FIG. 16 that has only one 4-F relay stage. In this case, as long as the shared lens 1604 is properly designed, the compensating lens 14102 and 15102 as shown in FIG. 14 and FIG. 15 can even possibly be replaced by a simple optical window 16106, although there can still be a need for a prism portion or a separate prism 16104 to direct the illumination beam as discussed before. Therefore, the definition of the compensating lens 14102/15102 should include even an optical window with an illumination beam bending portion as the concept of compensation should also include the optical function provided to the illumination beam. In addition, the top optical window can also be coated to only allow the visible spectrum of light to transmit through. In this manner, the near infrared spectral portion of light will not land on the patient eye to create eye returned near infrared background light that can enter the wavefront sensing detector to either saturate the detector or create background noise.

At this point, it should be noted that for the embodiments of FIGS. 14, 15, and 16, since the first lens at the input port of the wavefront sensor module is shared, it needs to pass both the visible and the near infrared spectrum of light and also preferably to introduce minimum additional aberration. A good choice for this lens is an achromatic lens that is designed to work over the visible and near infrared light spectrum. If needed, aspherized achromatic lens can be used. As a narrow band filter can be used in front of the second lens of the first 4-F relay stage, the second lens and the following lenses if any can be one designed for functioning only over the SLD source near infrared spectrum range. The lenses can be aspheric lenses.

Figure 17:
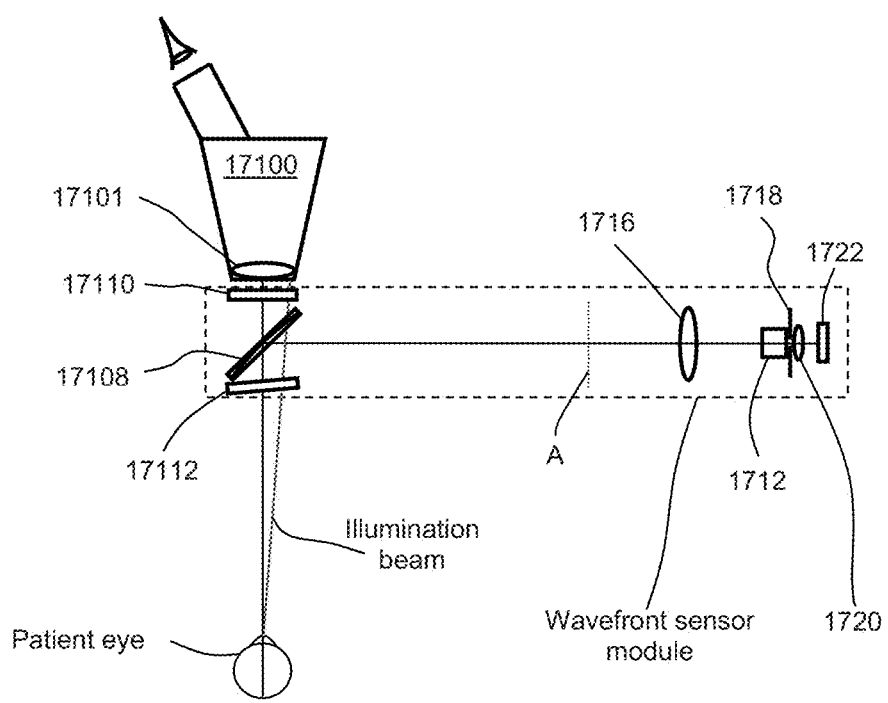
FIG. 17 shows another embodiment of wavefront integration with a microscope in which the dichroic or short pass beam splitter as shown in FIGS. 14, 15 and 16 is replaced by a specially made 45° near infrared focusing mirror (coated to reflect only the SLD spectrum) that acts as the first lens of the wavefront relay and also as a transparent plate to the visible spectrum for the surgical microscope.

As another alternative embodiment, the dichroic or short pass beam splitter 1461, 1561 and 1661 as shown in FIGS. 14, 15 and 16 can be replaced by a specially made 45° near infrared focusing mirror 17108 (coated to reflect only the SLD spectrum) to act as the first lens of the 4-F relay stage as shown in FIG. 17. Meanwhile it acts as a transparent plate to the visible spectrum for the surgical microscope. In this case, the original objective of the surgical microscope 17101 remains and the top and bottom optical windows 17110 and 17112 can be made from two glass plates with the bottom one tilted to direct specular reflection of the illumination light from the microscope away. Since the 45° near infrared focusing mirror 17108 is now functioning as the first lens of the 4-F relay and its axial position is moved further back from the patient eye, the second lens 1716 of the 4-F relay and the rest of the wavefront sensor optics need to be adjusted accordingly. The advantage of this embodiment is that the microscopic view will be minimally affected.

Figure 18:
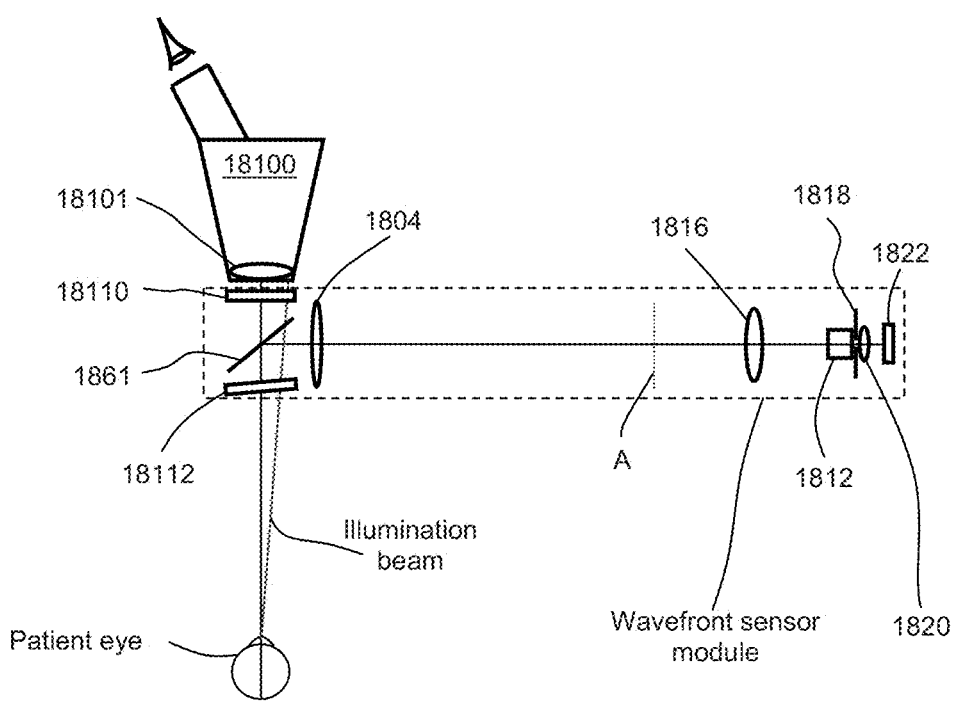
FIG. 18 shows another embodiment of the integration of the presently disclosed wavefront sensor module with a surgical microscope, in which a dichroic or short pass beam splitter is used to direct the near infrared wavefront beam to the wavefront sensor module and to pass the visible spectrum of light for the surgical microscope.

FIG. 18 shows another embodiment of the integration of the presently disclosed wavefront sensor module with a surgical microscope 18100. In this embodiment, a dichroic or short pass beam splitter 1861 is used to direct the near infrared wavefront beam of the SLD spectrum to the wavefront sensor module and to pass the visible spectrum of light for the surgical microscope. The bottom optical window 18112 can again be tilted to avoid specularly reflected visible light from getting into the microscope stereoscopic view. The top optical window 18110 can again be coated to allow the visible spectrum of light to transmit through. The first lens 1804 of the 4-F relay can be arranged as close to the eye as mechanically possible as long as it does get into the surgical microscope's illumination and viewing path. Due to the increased distance between the eye and the first lens 1804 of the 4-F relay, the second lens 1816 of the 4-F relay and the rest of the wavefront sensor optics need to be pushed back even further as compared to the previous cases. This can make the wavefront sensor module bulkier and the needed diameter of the first lens of the 4-F relay for covering the same diopter range of the eye wavefront will be larger. But the advantage is that the microscopic view will be even less minimally affected as compared to the other embodiments.

As an addition aspect of the present invention, in real disclosure, a diffusely reflective surface such as a spectralon plate can be dropped into the optical path to diffusively reflect the SLD beam to create a calibration wavefront that the wavefront sensor module can use for checking the optical alignment of the SLD beam and the optical alignment of the optical elements as well as the optical power of the SLD beam.

It should be noted that in all the embodiments, we have mentioned that the SLD spectrum is in the near infrared range. However, this should not be considered as a limitation because other spectrum range can be used. Although a near infrared light source for wavefront sensing is good in that it is not visible to the human eye, a visible light source for wavefront sensing is also good in the sense that the SLD beam can be directly used as the fixation light source or target and the wavefront measurement will be more accurate as the eye only sees visible light.

It should also be noted that the wavelength used for wavefront sensing and/or OLC/OCT measurements can be scanned or tuned. One benefit of tuning or scanning the wavelength is that chromatic aberration of the eye can also be measured. Another benefit is that by tuning the wavelength, spectroscopic measurement of the tissues of the eye, including the cornea, the eye lens, the vitreous, and even the retina or choroid can be determined. Still another benefit is that swept source based OLC/OCT detection scheme can be directly employed. The wavelength tuning can cover a large spectral range, including the whole visible spectral range and also the whole near infrared spectral range as needed.

The presently disclosed wavefront sensor module can be combined with a variety of other ophthalmic instruments for a wide range of applications. For example, it can be integrated with a femto-second laser or an excimer laser that is used for LASIK or eye lens fracturing as well as cornea incision/cutting. The live image, OLC/OCT, and the wavefront signal can be combined to indicate if optical bubble(s) or other optical non-uniformity is/are present in the eye lens or anterior chamber before, during and after an eye surgical operation. The wavefront information can also be used to directly guide the LASIK procedure in a closed loop manner.

The present invention can also be integrated or combined with an adaptive optics system. Deformable mirror or liquid crystal (LC) based transmissive wavefront compensator can be used to do real time wavefront manipulation to compensate the wavefront errors.

These embodiments could also be deployed to measure optics, spectacles/glasses, IOL and/or guide the cutting/machining devices that create the optics.

These embodiments could also be adapted to microscopes for cell and/or molecular analysis or other metrology applications.

The present invention can also be used for lens crafting, spectacle confirmation, micro-biology applications etc.

Although various embodiments that incorporate the teachings of the present invention have been shown and described in detail herein, those skilled in the art can readily devise many other varied embodiments that still incorporate these teachings.

What is claimed is:

1. A large diopter range sequential wavefront sensor for vision correction or assessment procedures comprising:
   a first optical wavefront relay system including first and second lenses, each lens having a diameter, a focal length and an optical axis, with the first optical wavefront relay system configured to relay an incident wavefront from a first object plane in a first object space to a first wavefront image plane in a first wavefront image space along a first beam path where the focal lengths and diameters of the first and second lenses are selected to guide an incident wavefront relay beam having a large diopter range at the first object plane to the first wavefront image plane;
   a second optical wavefront relay system including third and fourth lenses, each lens having a diameter, a focal length and an optical axis, with the second optical wavefront relay system having a second object plane in a second object space that is substantially at the first wavefront image plane, and configured to further relay the incident wavefront from the first wavefront image plane to a second wavefront image plane in a second wavefront image space along a second optical path, with the third lens configured to guide the wavefront relay beam to a Fourier transform plane located between the third and fourth lenses;
   a variable focal length lens disposed substantially at the second object plane in the second object space, with the variable focus length lens being substantially conjugate to the first object plane and the second wavefront image plane and configured to dynamically change the sphero-diopter value of the wavefront when it is relayed from the first object plane to the second wavefront image plane;
   a reflective beam shifting element disposed substantially at the Fourier transform plane located between the third and fourth lenses, positioned along the optical axis of the third lens to intercept substantially the entire wavefront relay beam over a desired large diopter range and oriented to fold the second optical path at a folding angle having a magnitude that prevents a wavefront beam reflected from being intercepted by the third lens;
   a wavefront sampling aperture positioned at or near the second wavefront image plane; and
   an image spot position sensing device positioned behind the sampling aperture.

2. A wavefront relay optical apparatus comprising:
   a first 4F optical relay including first and second lens and configured to relay a wavefront from a first object plane to a first image plane;
   a second 4F optical relay including third and fourth lenses configured to relay a wavefront from a second object plane to a second image plane, where the first and second 4F optical relays are disposed so that the second object plane and the first image plane are located at about the same position; and
   a variable focal length lens positioned substantially at the second object plane and configured to change the sphero-diopter value of the wavefront when it is relayed from the first object plane to the second wavefront image plane.

3. The wavefront relay optical apparatus of claim 2 wherein there is a Fourier transform plane in the second 4F optical relay and further comprising:
   a beam shifting element disposed at about the Fourier transform plane so that the beam shifting element intercepts substantially the entire wavefront relay beam.

* * * * *